United States Patent [19]

Teutsch et al.

[11] Patent Number: 4,912,097
[45] Date of Patent: Mar. 27, 1990

[54] NOVEL 11 β-ALKYNYLPHENYL-10-NOR-STEROIDS

[75] Inventors: Jean-Georges Teutsch, Pantin; Michel Klich, Villemomble; Daniel Philibert, La Varenne-Saint-Hilaire, all of France

[73] Assignee: Roussel Uclaf, Paris, France

[21] Appl. No.: 44,958

[22] Filed: Apr. 30, 1987

[30] Foreign Application Priority Data

May 6, 1986 [FR] France ................... 86 06517

[51] Int. Cl.4 ................... C07J 63/00; A61K 31/705; A61K 21/00; A61K 41/00
[52] U.S. Cl. ................... 514/172; 260/397; 260/397.1; 260/397.2; 260/397.3; 260/397.45; 260/397.5; 514/169; 514/173; 514/177; 514/179; 514/182; 540/4; 540/25; 540/29; 540/30; 540/32; 540/33; 540/41; 540/44
[58] Field of Search ................... 260/397, 397.2, 397.2, 260/397.3, 397.45, 397.5; 540/4, 25, 29, 30, 32, 33, 41, 44; 514/169, 172, 173, 177, 179, 182

[56] References Cited

U.S. PATENT DOCUMENTS 4,233,296  11/1980  Teutsch et al. ................... 514/172
4,386,085   5/1983  Teutsch ........................... 514/179
4,477,445  10/1984  Philibert et al. ................... 514/178

Primary Examiner—Mark L. Berch
Attorney, Agent, or Firm—Bierman & Muserlian

[57] ABSTRACT

Novel 11β-alkynylphenyl-19-nor-steroids of the formula

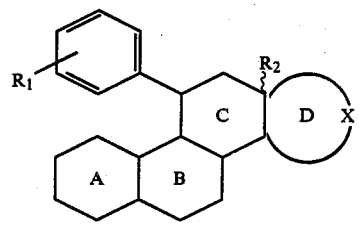

wherein $R_1$ is alkynyl of 2 to 8 carbon atoms optionally substituted with at least one member of the group consisting of —OH halogen, trialkylsilyl of 1 to 6 alkyl carbon atoms, alkoxy and alkylthio of 1 to 6 carbon atoms and dialkylamino of 1 to 6 alkyl carbon atoms having remarkably antiprogestomimetic and antiglucocorticoidal activity.

21 Claims, No Drawings

NOVEL 11 β-ALKYNYLPHENYL-10-NOR-STEROIDS

STATE OF THE ART

Related patents include U.S. Pat. No. 4,386,085; No. 4,477,445 and No. 4,233,296 and European Pat. No. 104,387 and Adrenal. Steroids Antagonism M. K. Agrawal Editor, Walter Degruyter & Co., p. 43–75 (1984).

OBJECTS OF THE INVENTION

It is an object of the invention to provide the novel compounds of formula I and their non-toxic, pharmaceutically acceptable salts and a process for their preparation.

It is another object of the invention to provide novel antiprogestomimetic and antiglucocorticoidal compositions and a method of inducing antiprogestomimetic and antiglucocorticoidal activity in warm-blooded animals.

These and other objects and advantages of the invention will become obvious from the following detailed description.

THE INVENTION

The novel compounds of the invention are selected from the group consisting of 11β-alkynylphenyl-19-nor-steroids of the formula

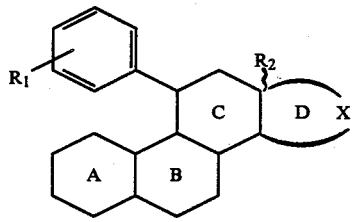

I wherein $R_1$ is alkynyl of 2 to 8 carbon atoms optionally substituted with at least one member of the group consisting of —OH, halogen, trialkylsilyl of 1 to 6 alkyl carbon atoms, alkoxy and alkylthio of 1 to 6 carbon atoms and dialkylamino of 1 to 6 alkyl carbon atoms, $R_2$ is alkyl of 1 to 3 carbon atoms, the A and B rings have a structure selected from the group consisting of

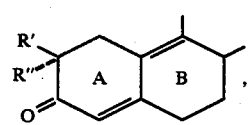  (A)

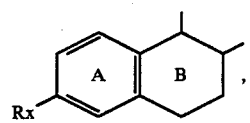  (B)

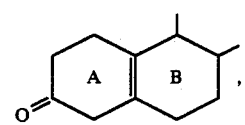  (C)

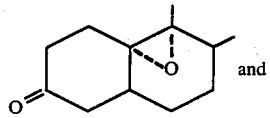  (D)

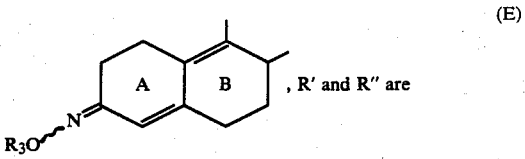  (E)

, R' and R" are individually selected from the group consisting of hydrogen and alkyl of 1 to 4 carbon atoms, Rx is selected from the group consisting of hydrogen, or ORe in which Re is selected from the group consisting of hydrogen, optionally substituted alkyl of 1 to 6 carbon atoms and acyl, $R_3$ selected from the group consisting of hydrogen, alkyl of 1 to 8 carbon atoms and aralkyl of 7 to 15 carbon atoms, the group

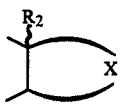

is selected from the group consisting of

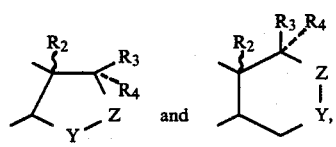

$R_3$ and $R_4$ are individually selected from the group consisting of hydrogen, optionally acylated or etherified hydroxy, alkyl of 1 to 8 carbon atoms, alkenyl and alkynyl of 2 to 8 carbon atoms, carbocyclic aryl, heterocyclic aryl, aralkyl, aralkenyl and aralkynyl, the latter five being optionally substituted with at least one member of the group consisting of hydroxy, alkoxy and alkylthio of 1 to 4 carbon atoms, halogen and dialkylamino of 1 to 6 alkyl carbon atoms or $R_3$ and $R_4$ taken together form a member of the group consisting of

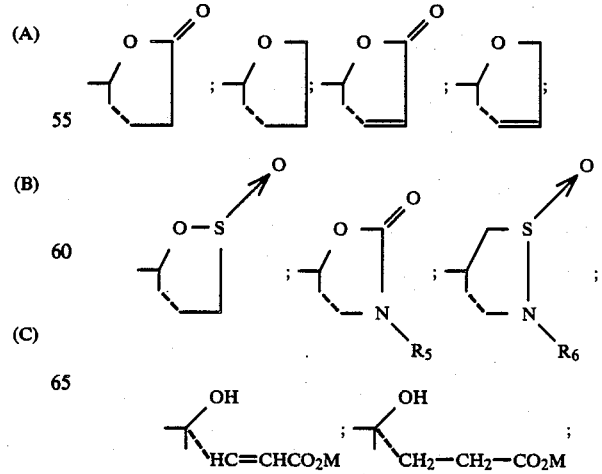

-continued

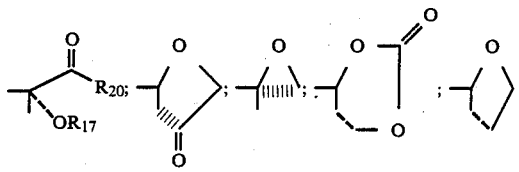

$R_5$ and $R_6$ are hydrogen or alkyl of 1 to 4 carbon atoms, M is hydrogen, lithium, sodium or potassium, $R_{20}$ is optionally substituted alkyl of 1 to 8 carbon atoms, $R_{17}$ is selected from the group consisting of hydrogen and acyl, X and Y form a group selected from the group consisting of

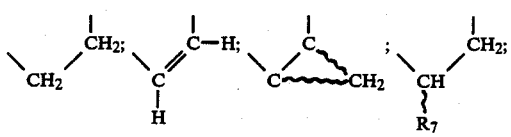

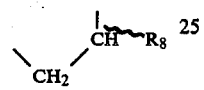

$R_7$ and $R_8$ are individually alkyl of 1 to 4 carbon atoms and the wavy lines indicate that $R_2$ $R_7$, and $R_8$ can be in either possible configuration and their non-toxic, pharmaceutically acceptable salts with acids and bases.

Examples of $R_1$ are ethynyl, propynyl, butynyl, pentynyl or hexynyl, preferably —C≡C—$R_{1a}$ wherein $R_{1a}$ is hydrogen or alkyl of 1 to 6 carbon atoms such as methyl, ethyl, propyl, isopropyl, butyl, secondary butyl or tert-butyl. Most preferred possibility for $R_1$ is ethynyl in the para position. The alkynyl groups may be substituted by hydroxyl or halogen such as fluoro, chloro, bromo, iodo, and preferably chloro, trialkylsilyl preferably trimethylsilyl, or alkoxy, alkylthio or dialkylamino such as methoxy, ethoxy, methylthio, ethylthio, dimethylamino or oxo.

$R_2$ may be methyl, ethyl or propyl and preferably methyl or ethyl, most preferably methyl. R' and R" may be methyl, ethyl, propyl, isopropyl or linear, secondary or tertiary butyl radical. Preferably R' and R" are both hydrogen.

Re may be any of the alkyl possibilities mentioned above and when this alkyl is substituted, it can especially be substituted by dialkylamino such as dimethylamino, diethylamino or methylethylamino. The acyl which Re may be is preferably acetyl or propionyl.

Examples of $R_3$ or $R_4$ are the alkyl mentioned above and preferably propyl. $R_3$ and $R_4$ which can be the same or different can also be hydrogen or OH, OAlk$_4$ or O—CO—Alk$_5$, Alk$_4$ and Alk$_5$ being an optionally-substituted alkyl of 1 to 8 carbon atoms or an optionally-substituted aralkyl of 7 to 15 carbon atoms, or $R_3$ and $R_4$ may be an optionally-substituted alkenyl or alkynyl of 2 to 8 carbon atoms.

$R_3$ and $R_4$ may also be carbocyclic aryl or aralkyl optionally-substituted with a member of the group consisting of hydroxy, alkoxy, alkylthio and dialkylamino and halogen. $R_3$ and $R_4$ are preferably phenyl, benzyl or phenethyl optionally-substituted by methoxy, methylthio, chloro, fluoro or hydroxy. $R_3$ and $R_4$ may also be heterocyclic arylor aralkyl such as thienyl or furyl optionally having the same substituents as those indicated above.

When $R_3$ and $R_4$ are OAlk$_4$ or OCOAlk$_5$, Alk$_4$ and Alk$_5$ preferably are methyl, ethyl, n-propyl, butyl, pentyl, hexyl or benzyl radical. When $R_3$ or $R_4$ are alkenyl, it is preferably vinyl, isopropenyl, allyl 2-methylallyl or prop-1-enyl, the last-mentioned substituent being preferred. When $R_3$ or $R_4$ are alkynyl, it is preferably —C≡CH or —C≡C—Alk$_9$, Alk$_9$ preferably being methyl, ethyl, propyl, isopropyl, isopropenyl, butyl, benzyl or trifluoromethyl, again preferably methyl.

When $R_3$ or $R_4$, preferably $R_4$ is a substituted alkyl, alkenyl or alkynyl, it is preferably propyl, propenyl or propynyl substituted by halogen such as chloro and most preferably by hydroxyl. The preferred possibility for $R_{20}$ is methyl optionally substituted by hydroxyl. $R_{17}$ is preferably hydrogen or acetyl.

Alk$_6$ preferably is one of the preferred possibilities for Alk$_4$ or Alk$_5$ and Alk$_6$ is preferably methyl or hydroxymethyl. When $R_3$ or $R_4$ is aralkynyl it is preferably pyridylethynyl such as 2-pyridylethynyl. The preferred compounds are those in which $R_3$ and $R_4$ are different.

Amongst the preferred possibilities for the

are

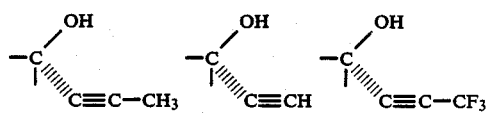

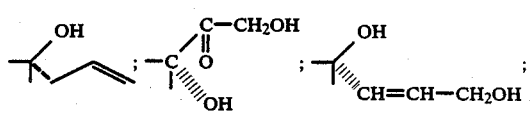

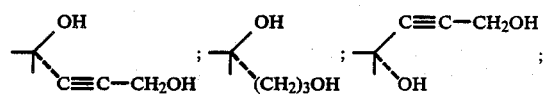

E or Z, preferably Z;

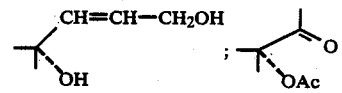

Taking account of the different possibilities for Y and Z, the D ring can preferably be the following:

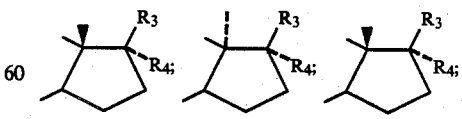

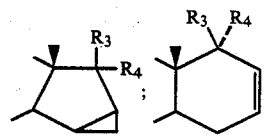

Taking account of the combination of the possibilities for $R_3$ and $R_4$ and of the possibilities for Y and Z, the following possibilities can be regarded as preferred for the D ring:

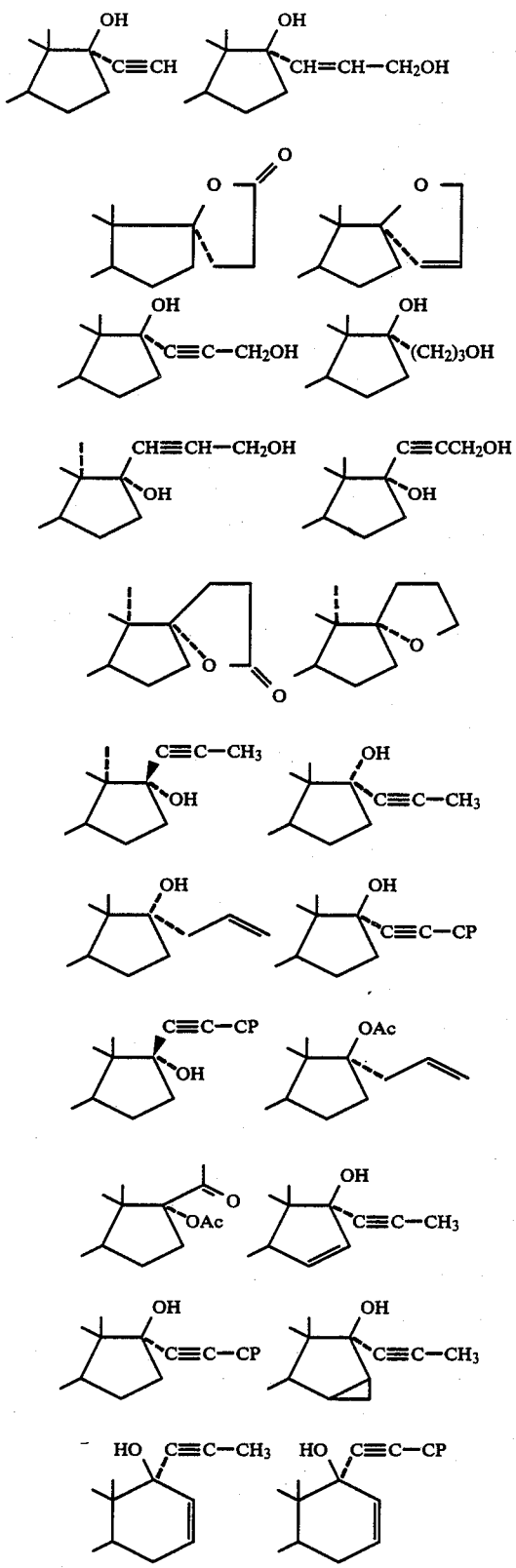

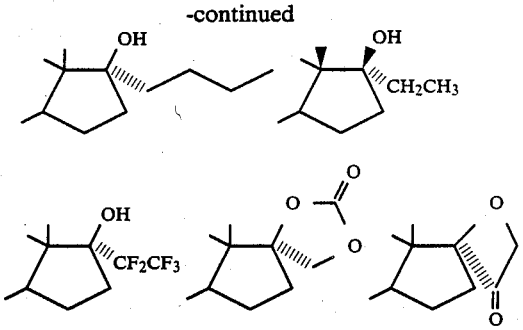

The products of formula I having one or more functions capable of salt-formation with an acid can exist in the form of salts with acids such as for example the salts formed with hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid and aspartic acid, alkane sulfonic acids such as methane or ethane sulfonic acids and arylsulfonic acids such as benzene or p-toluene sulfonic acids and arylcarboxylic acids.

The products of formula I having one or more functions capable of salt-formation with a base can exist in the form of salts with bases such as the salts formed with an equivalent of sodium, potassium, lithium, calcium, magnesium or ammonium. Among the organic bases are methylamine, propylamine, trimethylamine, diethylamine, triethylamine, N,N-dimethylethanolamine, tris(hydroxy methyl)amino methane, ethanolamine, pyridine, picoline, dicyclohexylamine, morpholine, benzylamine, procaine, lysine, arginine, histidine and N-methylglucamine.

Among the preferred compounds of the invention are those of the formula

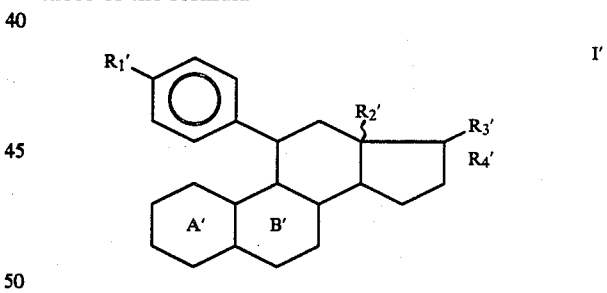

wherein $R_1'$ is alkynyl of 2 to 4 carbon atoms optionally-substituted by a member selected from the group consisting of hydroxy, halogen or trimethylsilyl; $R_2'$ is methyl or ethyl, $R_3'$ and $R_4'$ are an optionally acylated hydroxyl or alkyl, alkenyl or alkynyl radical having at most 8 carbon atoms and optionally substituted by a radical selected from the group consisting of hydroxyl or halogen, or $R_3'$ and $R_4'$ together form

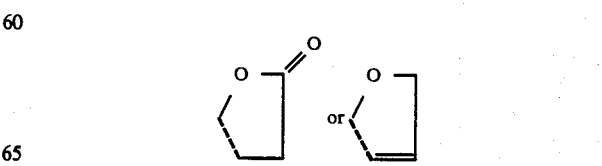

the A' and B' rings have a structure selected from the group consisting of (a)
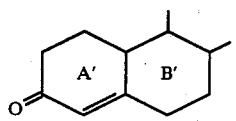

(b)
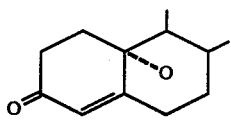

and (c)
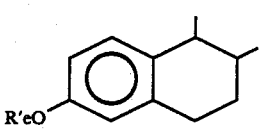

wherein R'e is hydrogen or alkyl of 1 to 4 carbon atoms.

The preferred possibilities for the radical $R_1'$ are ethynyl, propynyl or trimethylsilylethynyl, preferably ethynyl, $R_2'$ is preferably methyl, $R_3'$ is preferably hydroxyl or acetoxy, $R_4'$ is propynyl, propenyl, chloroethynyl or hydroxy prop-1-enyl or $R_4'$ can be hydroxyl when $R_3'$ is ethynyl, propynyl or chloroethynyl.

Among the products of formula I', another class of preferred compounds are those wherein $R_1'$ is —C≡C—$R_{11}$ and $R_{11}$ is hydrogen or methyl or trimethylsilyl, $R_3'$ and $R_4'$ are selected from hydroxyl, acetoxy, ethynyl and propynyl optionally-substituted by halogen or hydroxyl, propyl and propenyl optionally-substituted by hydroxy, or $R_3'$ and $R_4'$ together form

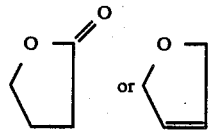

Specific preferred compounds are 11β-(4-ethynylphenyl)-17α-(1-propynyl)-Δ$^{4,9}$-estradien-17β-ol-3-one, 11β-(4-ethynylphenyl)-17α-allyl-Δ$^{4,9}$-estradien-17β-ol-3-one, 17α-(chloroethynyl)-11β-(4-ethynylphenyl)-Δ$^{4,9}$-estradien-17β-ol-3-one and 17α-(chloroethynyl)-9α-, 10α-epoxy-11β-(4-ethynylphenyl)-Δ$^4$-estren-17β-ol-3-one.

The novel process of the invention for the preparation of the compounds of formula I comprises reacting a compound of the formula II
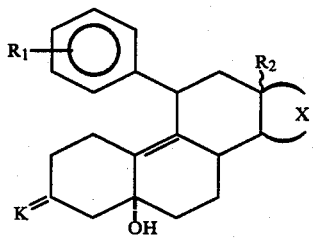

wherein K is a blocked ketone function, and $R_1$ and $R_2$ and X have the above definitions with a dehydration reagent capable of liberating the ketone function to obtain a compound of the formula $I_A$
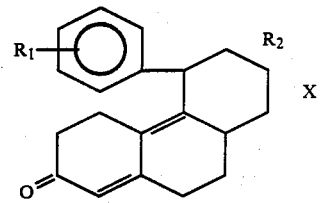

and optionally subjecting the latter (a) either to the action of a reducing agent, then to an acid aromatization agent to obtain a product of formula $I_{B1}$ wherein A and B are

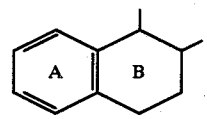

(b) or to the action of an aromatization agent, then a saponification agent and then optionally an alkylation or acylation reagent to obtain a product of formula $I_{B2}$ in which A and B are

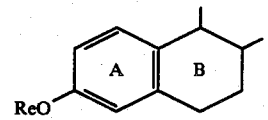

and Re has the above definition:

(c) or to the action of a reducing agent to obtain a product of formula $I_C$ in which A and B are

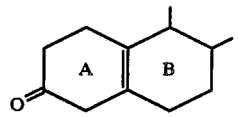

(d) or to the action of an oxidation agent to obtain the products of formula $I_D$ in which A and B are:

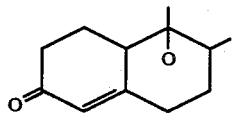

(e) or to the action of hydroxylamine, either free as $NH_2OH$ or blocked in the form $NH_2OR_3'$ wherein $R_3'$ is alkyl of 1 to 8 carbon atoms or aralkyl of 7 to 15 carbon atoms to obtain the products of formula $I_E$ in which A and B are:

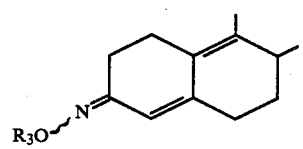

and optionally products of formula $I_A$, $I_{B1}$, $I_{B2}$, $I_C$, $I_D$ and $I_E$ may be subjected to the action of an acid to obtain a salt.

K preferably is a ketal or cyclic ketal such as dimethyl or diethylketal, ethylenedioxy or a thioketal.

In a preferred manner of carrying out the process, the dehydration agent capable of liberating the ketone function is a sulfonic acid resin (acid form), for example a commercially-available sulfonic resin on a polystyrene support or on a styrene-divinylbenzene polymer support. However, equally useful is a mineral acid such as hydrochloric acid or sulfuric acid in a lower alkanol, or perchloric acid in acetic acid, or a sulfonic acid such as p-toluene sulfonic acid.

During the dehydration reaction, the protective groups which the products of formula II may contain are generally eliminated. This is specifically so with protective groups for the hydroxy function which the substituents $R_3$ and $R_4$ at the 17 position may bear. If this is not the case, the protective groups can be eliminated by conventional methods such as alkaline hydrolysis. The reduction agent to prepare the product of formula $I_{B1}$ is preferably an alkali metal borohydride such as sodium borohydride and one operates in an alkanol such as methanol or ethanol to obtain an intermediate product in which A and B are:

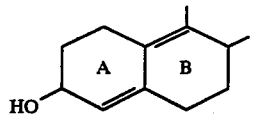

The aromatization agent preferably employed to prepare the products of formula $I_{B1}$ is a mineral acid such as hydrochloric acid or sulfuric acid, or alternatively an agent such as phosphorus pentachloride, phosphorus tribromide or phosphorus oxychloride, or alternatively an anhydride such as acetic or trifluoroacetic anhydride. The aromatization agent preferably used to prepare the products of formula $I_{B2}$ is an acyl halide, for example acetyl bromide or acetic anhydride or a mixture of these products.

The saponification agent employed is preferably an alkali metal base such as sodium hydroxide or potassium hydroxide, sodium amide, potassium tert-butylate or lithium acetylide in ethylenediamine. The reaction takes place preferably in a lower alcohol such as methanol or ethanol. Depending on the conditions employed and in the case where for example, the

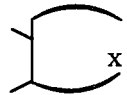

substituent contains a reactive function, for example a 17β-hydroxy, one may get partial acetylation of this function. Then, besides the expected 17β-OH product, one recovers a variable percentage of the 17β-OAc. These 17β-OH and 17β-OAc products can be separated by conventional methods such as chromatography.

The optional alkylation is carried out by conventional methods and the alkylation reagent is preferably an alkyl halide such as alkyl iodide or alkyl sulfate, preferably methyl sulfate. The acylation equally is performed by the conventional methods, preferably with an acyl halide.

The reduction agent used to convert the products of formula $I_A$ into products of formula $I_C$ is preferably an alkali metal in liquid ammonia, preferably lithium, but sodium equally can be used. Dependent on the quantities of metal employed, modifications at other points upon the molecule can be made.

The oxidation agent used to prepare a product of formula $I_D$ is preferably a peracid such as meta-chloroperbenzoic acid, peracetic acid or perphthalic acid or alternatively hydrogen peroxide alone or in the presence of hexachloro- or hexafluoro-acetone. The action of the hydroxylamine or a derivative thereof is carried out under conventional conditions.

In a variation of the process, a product of formula $I_A$, $I_{B1}$, $I_{B2}$, $I_C$, $I_D$ and $I_E$ containing upon the D ring an alkynyl is subjected to the action of a reducing agent to obtain the corresponding alkenyl compound. In another variation of the process, a product of formulae $I_A$, $I_{B1}$, $I_{B2}$, $I_C$ and $I_D$ containing on the D ring:

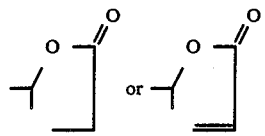

is subjected to the action of an alkali metal hydroxide or of ammonia, then optionally to the action of an acid reagent to obtain a product containing

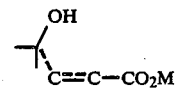

in which the dotted line indicates the optional presence of a second bond and M has the above meaning. Such a reaction has been described for example in French Patent No. 2,496,669.

The invention also is directed to a process for the preparation of the products of formula I containing an acyloxy characterized in that a product of formulae $I_A$, $I_{B1}$, $I_{B2}$, $I_C$, $I_D$ or $I_E$ containing a free hydroxy is reacted with a carboxylic acid derivative. In a preferred manner of carrying out this process, the product to be acylated is reacted with a derivative such as a symmetric anhydride or an acid chloride in the presence of pyridine or of 4-dimethylaminopyridine or with an acid catalyst such as p-toluene sulfonic acid.

The invention has more especially as its object a process for the preparation of products of formulal I' as defined above comprising carrying out the previously described process starting from a product of the formula

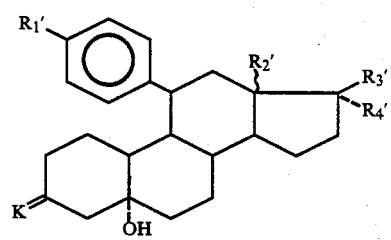

II' in which K, $R_1'$, $R_2'$, $R_3'$ and $R_4'$ have the above definitions.

The invention equally has as its object a process wherein the starting product of formula II is prepared either by subjecting a product of formula III

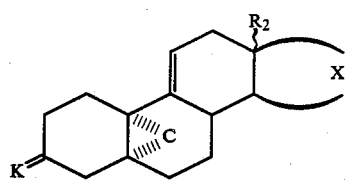 III to the action of a product chosen from the group consisting of the products of formula

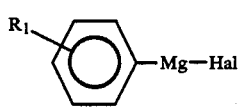

and of formula

in which $R_1$ has the above meaning and Hal is halogen, if required, in the presence of cuprous halide: or by subjecting a product of the formula

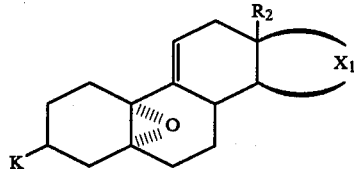 IV in which

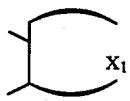

is either:

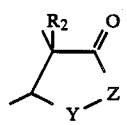

or:

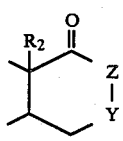

in which $R_2$, Y and Z have the above meaning to the action of a product chosen from the group consisting of

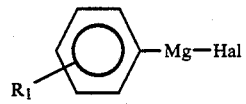

and of the formula

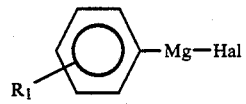

in which $R_1$ and Hal have the above meanings, if required, in the presence of cuprous halide to obtain a product of the formula

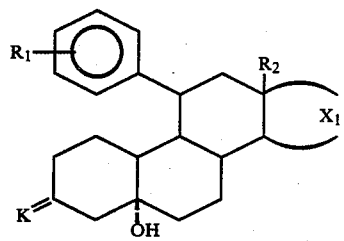 $V_A$ and optionally subjecting the latter to the action of ultra-violet irradiation to obtain a product of the formula

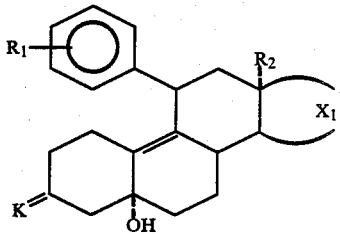 $V_B$ and subjecting the products of formulae $V_A$ or $V_B$ to one of the following reactions:

(a) or a product of formulae $V_A$ or $V_B$ is reacted with H—C≡C—CH$_2$—O—Gp in which Gp is a protective group for hydroxyl to obtain a product of the formula

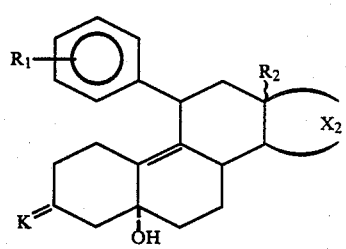 VI in which in which

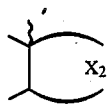

X₂ is

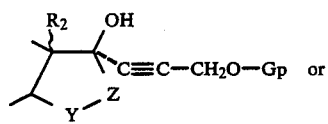

or

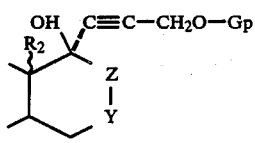

and reacting the latter product with a reduction agent, then with a deblocking agent for the hydroxyl to obtain a product of the formula

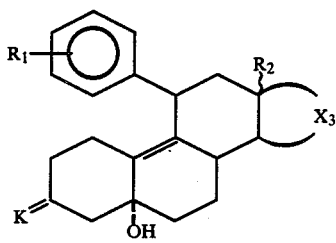

VII in which

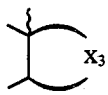

X₃ is

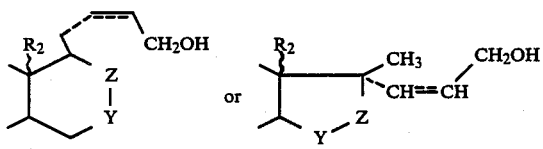

the dotted line indicating the possible presence of a second bond E or Z between the carbons, reacting the latter either with an oxidation agent to obtain a product of the formula

II_A

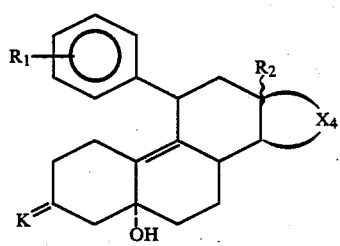

in which X₄ is

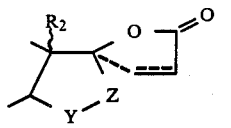 or 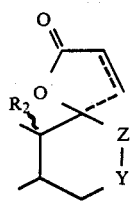

in which the dotted line indicates the possible presence of a second bond between the carbon atoms or the product of formula VII is reacted with a cyclization reagent to obtain a product of the formula

II_B

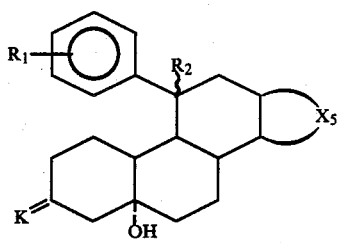

in which

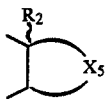

X₅ is

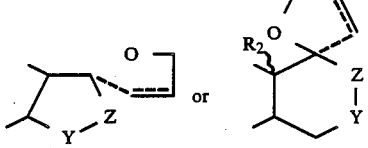

in which the dotted line indicates the possible presence of a second bond between the carbon atoms.

(b) or a product of formulae V_A or V_B is first reacted with an oxirane-formation reagent, then with a product of the formula

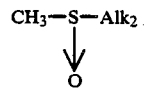

in which Alk₂ is alkyl of 3 to 5 carbon atoms, and finally with a cyclization reagent to obtain a product of the formula

15

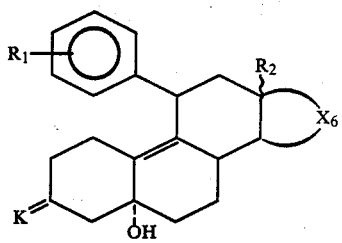

in which:

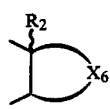

is

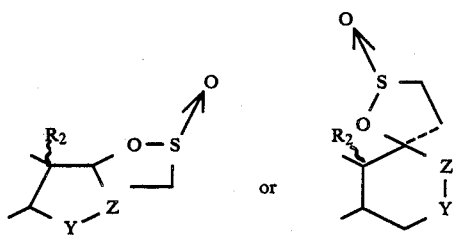

(c) or a product of $V_A$ or $V_B$ is first reacted with an oxirane-formation reagent, then with an alkylamine of the formula $H_2NR_5$, $R_5$ having the above meaning, and finally with a carbonic acid derivative, to obtain a product of the formula

II$_D$

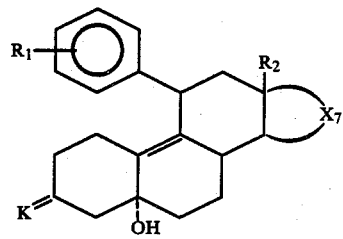

in which:

is

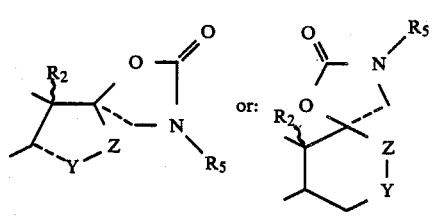

(d) or a product of formulae $V_A$ or $V_B$ is first reacted with an oxirane-formation reagent, then with an alkyla-

16 mine of the formula $H_2NR_5$, and finally with thionyl chloride to obtain a product of the formula

II$_E$

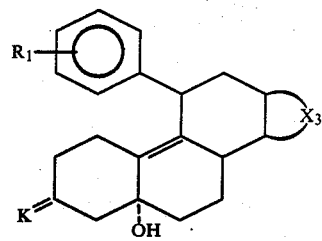

in which:

is

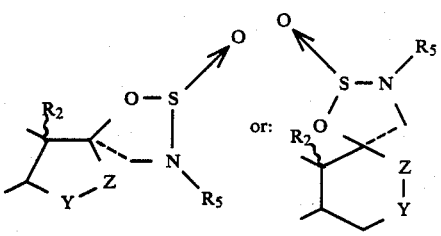

(e) or a product of formulae $V_A$ or $V_B$ is reacted with an organomagnesium or an organolithium compound to obtain a product of the formula

II$_F$

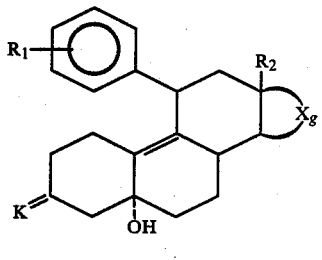

in which:

is

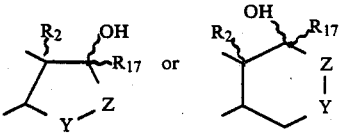

in which $R_{17}$ is alkyl, alkenyl or alkynyl radical having at most 8 carbon atoms, or a carbocyclic aryl or heterocyclic aryl, aralkyl, aralkenyl or aralkynyl, all optionally substituted with at least one member of the group consisting of hydroxy, alkoxy or alkylthio of 1 to 4 carbon atoms or halogen.

(f) or a product of formulae $V_A$ or $V_B$ is either reacted with a cyanization agent, then with a protection agent for the hydroxy, and then finally with a magnesium or a lithium agent, or is reacted with a lithium agent of the formula

in which $Alk_f$ is alkyl of 1 or 4 carbon atoms, then to the action of a base and of an acid to obtain a product of formula

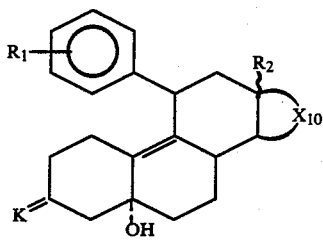

in which

is

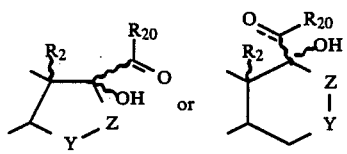

in which $R_{20}$ is an optionally substituted alkyl, which is optionally reacted with an acylation reagent.

(g) or a product of formulae $V_A$ or $V_B$ is reacted with trimethylsulfonium halide or $CH_2-S^+-(CH_3)_2$ in the presence of a strong base to obtain a product of the formula

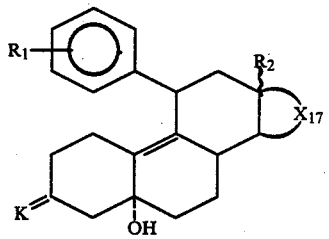

in which

is

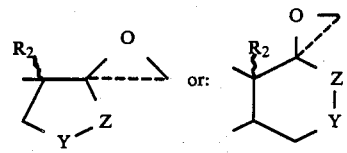

and the product of formula $II_H$ is optionally reacted with a product of formula $CH_2^--S^+-(CH_3)_2$ to obtain a product of the formula

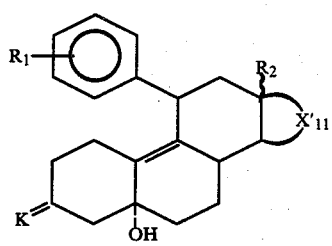

in which

is

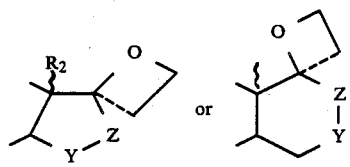

and the product of formula $II_H$ is optionally subjected first to alkaline hydrolysis, then to the action of a product of the formula $Hal-CO_2Alk_g$ in which Hal is halogen and $Alk_g$ is alkyl of 1 to 4 carbon atoms, and finally to the action of a dialkyl carbonate to obtain a product of the formula

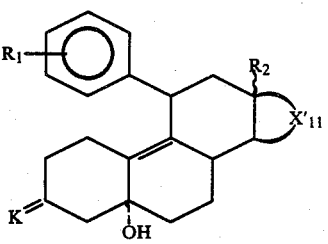

in which is

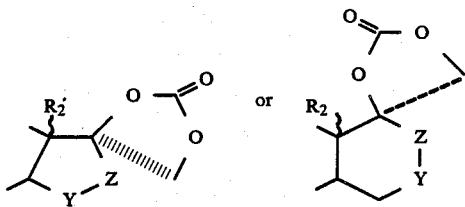

(h) or a product of formulae $V_A$ or $V_B$ is first reacted with a lithium reagent of formula

in which $Alk_h$ is alkyl of 1 to 4 carbon atoms, then to the action of a halogenation reagent, then finally the action of a base to obtain a product of the formula

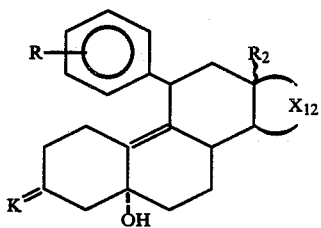

$II_J$ in which

is

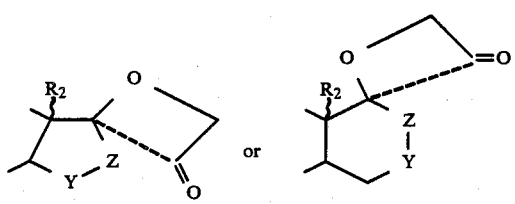

In a preferred method of the process, the reaction of the products of formulae

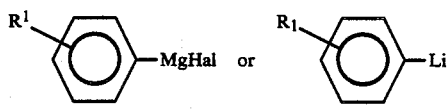

takes place at ambient temperature and with a magnesium reagent, the reaction takes place preferably in the presence of cuprous salts such as cuprous chloride.

The conversion of the products of formula $V_A$ into the products of formula $V_B$ is carried out with good yield conditions and the duration of exposure to the ultra-violet lamp can be on the order of 10 minutes up to an hour. One preferably used is a mercury quartz lamp at high pressure and for example, at ambient temperature in a solvent such as dioxane, cyclohexane, benzene, toluene or tetrahydrofuran or in a mixture of solvents. The concentration of the product to be converted can be on the order of 1% by weight or less. After the reaction, the products can be purified by chromatography or by any other known method of purification.

The reaction of the product of formula $H-C{\equiv}C-CH_2OG_p$ is preferably effected with a metallic derivative such as that of lithium and for example, as indicated in European Patent Application No. EP 0,116,974 in the presence of butyl lithium. The protective grouping $G_p$ is preferably tetrahydropyranyl.

The reduction of the products of formula VI containing a $17\alpha-C{\equiv}C-CH_2OG_p$ can be carried out by means hydrogen at normal pressure and at ambient temperature in a solvent such as methanol, ethanol, propanol, ethyl acetate or tetrahydrofuran in the presence of a metallic catalyst such as 10% palladium on charcoal to obtain the products of formula VII in which there is no unsaturation in the 17-substituents.

To obtain the products of formula VII containing $17\alpha$-alkenyl, one operates under the conditions specified for example in European Patent Application No. EP 0,147,361. The products of the Z configuration are obtained by hydrogenating the acetylenic products with a deactivated metallic catalyst such as for example 10% palladium on barium sulfate in the presence of an amine, or palladium on calcium carbonate in the presence of lead acetate. The products of the E configuration are obtained by methods known from the literature such as for example sodium in liquid ammonia or lithium in an amine.

The elimination of the protective grouping $G_p$, if it has not taken place in the course of the hydrogenation reaction, is effected by conventional methods such as for example by acid hydrolysis in the presence of acetic acid or hydrochloric acid in aqueous solution at ambient temperature or at a temperature of about 50° C.

The oxidation reagent to prepare the products of formula $II_A$ can be selected from among the known reagents summarized for example in European Patent Application No. EP 0,116,974 with the aid of the Jones reagent: chromic anhydride in dilute sulfuric acid, pyridinium dichromate or chlorochromate, silver carbonate in the presence of celite, oxygen in the presence of platinum or the pyridine-chromic-acid complex.

The cyclization of the products of formula VII into products of formula $II_B$ is carried out with a reagent such as for example tosyl chloride in the presence of pyridine.

The preparation of the sultines of formula $II_C$ can be effected in accordance with the conditions described in French Patents No. 2,285,137 and No. 2,344,286. The formation of the oxirane is preferably effected with trimethyl sulfonium iodide in the presence of a strong base such as potassium tert-butylate. The addition of the product of formula

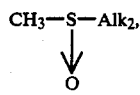

preferably methyltert-butylate sulfoxide, is equally effected in the presence of a strong base for example butyl lithium. The cyclization reagent is preferably N-chloro or N-bromo succinimide and the reaction can take place at ambient temperature in the presence of water.

The preparative reaction for the products of formula $II_D$ is effected by preparing the oxirane under the previously indicated conditions and the alkylamine $H_2NR_5$, preferably methylamine, can be added in the presence of p-toluene sulfonic acid, at high temperature. The derivative of carbonic acid then used is preferably the dimethyl ester and the reaction carries itself to reflux, preferably in the presence of a strong base such as potassium tert-butylate. For the preparation of the products of formula $II_E$, at the end reaction, thionyl chloride is preferably used in the presence of triethylamine.

For the preparation of the products of formula $II_F$, the conventional conditions specifically described above and equally appearing for example in European Patent Nos. EP 0,057,115 and EP 0,116,974 are used for example in the presence of butyl lithium.

For the preparation of the products of formula $II_G$ with a cyanization agent, then with a protection agent for the hydroxy and then finally with a magnesium or lithium agent, the conventional conditions are used. In a preferred method of preparation, the cyanization agent is potassium cyanide and the protection agent for the hydroxy is preferably trichloromethylsilane. The preparation of such products is described for example in French Patent No. 2,082,129. The optional acylation is carried out under conventional conditions described hereinabove.

The lithium reagent of the formula

is preferably the lithium derivative of vinyl ethyl ether and the reaction is in tetrahydrofuran. The base is preferably sodium hydroxide in methanol, and the acid is hydrochloric acid in methanol. The products of formula $II_G$ can equally be prepared by hydration in the presence of mercuric salts of a product of formula $II_F$ in which $R_{17}$ is $-C\equiv CH$.

The preparation of the products of formula $II_H$ is effected by conventional methods. The strong base one may be an alkali metal alcoholate such as sodium methylate or potassium tert-butylate or an alkali metal hydride such as sodium hydride. The reaction conditions are the same.

The preferential operating conditions for preparing the products of formula $II_H''$ are described for example in the publication Act. Chim. Hung., 1984, 116(2) 111-23 (CA Vol. 101, 1984, p. 801 No. 192272 p.). The product of formula $II_H$ is subjected to alkaline hydrolysis; the product of formula Hal—$CO_2$—$Alk_g$ reacting upon the diol is Cl—$CO_2$—Et preferably in a solvent such as pyridine and the dialkyl carbonate is preferably diethyl carbonate in the presence of metallic sodium.

The preparation of the products of formula $II_J$ is effected preferably first with vinylethyl ether lithium, then with N-bromo succinimide, and then finally with a base such as sodium hydroxide.

The novel anti-progestomimetic and antiglucocorticoid compositions of the invention are comprised of an anti-progestomimetically and anti-glucocorticidally effective amount of at least one compound of formula I and its non-toxic, pharmaceutically acceptable salts and an inert pharmaceutical carrier or excipient. The compositions may be in the form of tablets, dragees, capsules, granules, suppositories lotions, creams, gels and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffinic derivatives, glycols, various wetting agents, dispersants or emulsifiers, and preservatives.

The compositions in tests on hormonal receptors show progestomimetic or anti-progestomimetic, androgenic or anti-androgenic activity. They possess a remarkable anti-progestomimetic activity as well as anti-glucocordicoid activity. Some of the compounds have a greater anti-progestomimetic activity than anti-glucocorticoid activity.

Due to their anti-progestomimetic activity, the compositions are useful as contraceptives, to combat hormonal irregularities and to treat hormonal dependent cancers. Due to their anti-glucocorticoid activity, the compositions are also useful to counteract the secondary effects of glucocorticoids, to counteract ailments due to hypersecretion of glucocorticoids and specifically against aging generally and especially against hypertension, atheroslerosis, osteoporosis, diabetes, obesity and immunodepression and insomnia.

Some of the compounds of formula I and their salts also display progestomimetic properties and can be used to treat amenorrhoea, dysmenorrhoea and luteak insufficiencies.

The compounds of formula I and their salts with antiandrogenic activity are useful in the treatment of hypertrophy, prostrate cancer, hyperandrogenia, anemia, hirsutism and acne.

Among the preferred compositions of the invention are those containing as the active ingredient 11β-(4-ethynylphenyl)-17α-(1-propynyl) $\Delta^{4,9}$-estradien-17β-ol-3-one, 11β-(4-ethynylphenyl)-17α-allyl-$\Delta^{4,9}$-estradien-17β-ol-3-one, 17α-(chloroethynyl)-11β-(4-ethynylphenyl)-$\Delta^{4,9}$-estradien-17β-ol-3-one or 17α-(chloroethynyl)-9α,10α-epoxy-11β-(4-ethynylphenyl)-$\Delta^4$-estren-17β-ol-3-one.

The novel method of the invention for inducing anti progestomimetic and anti-glucocorticoid activity in warm-blooded animals, including humans, comprises administering to warm-blooded animals an anti-progestomimetically and anti-glucocorticoidally effective amount of at least one compound of formula I and its non-toxic, pharmaceutically acceptable salts with acids and bases. The compounds may be administered orally, rectally, parenterally or topically.

The products of formulae III or IV are known or can be prepared by conventional methods starting from known products for example, in European Patent Applications No. EP 0,116,974 or EP No. 0,156,284.

The products of formula III can also be prepared by reacting a product of the formula

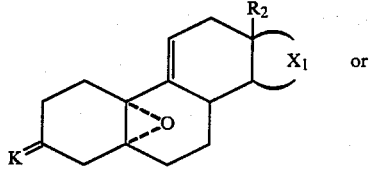
(IV)

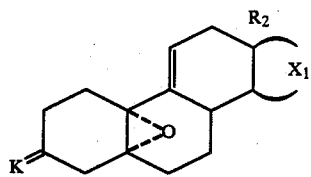
(IV$_B$)

wherein K, $R_2$ and $X_1$ have the above meaning to the various reactions described herein above for the products $V_A$ AND $V_B$. Products $IV_B$ can be obtained as previously described starting from the products of formula IV.

Examples of compounds of the invention are illustrated in the following Tables.

(A) The products of the formula

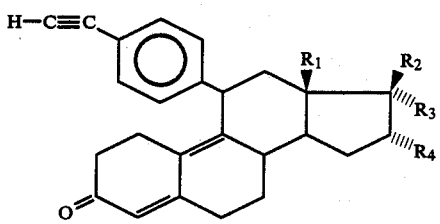

| $R^1$ | $R^2$ | $R^3$ | $R^4$ |
|---|---|---|---|
| CH$_3$ | OH | C≡C—H | H |
| " | " | C≡C—CH$_2$CH$_3$ | H |
| " | " | C≡C—(CH$_2$)$_2$CH$_3$ | H |
| " | " | C≡C—C(CH$_3$)=CH$_2$ | H |
| " | " | C≡C—Ph | " |
| " | " | C≡C—CF$_3$ | " |
| " | " | C≡C—CF$_2$CF$_3$ | " |
| " | " | CH=CH$_2$ | " |
| " | " | CH$_2$—CH$_3$ | " |
| " | " | CH$_3$ | " |
| " | " | CH$_2$CH$_2$OH | " |
| " | " | CH$_2$CH$_2$CH$_2$OH | " |
| " | " | CH=CH—CH$_3$ (E) | " |
| " | " | CH=CH—CH$_3$ (Z) | " |
| " | " | CH$_2$—C(CH$_3$)=CH$_2$ | " |
| " | " | Ph | " |
| " | " | CF$_2$CF$_3$ | " |
| " | " | CH$_2$Ph | " |
| " | " | CH$_2$CH$_2$—CO$_2$H | " |
| " | " | C≡C—SCH$_3$ | " |
| " | " | C≡C—SPh | " |
| " | " | CH=C=CH$_2$ | " |
| " | " | CH$_2$C≡C—H | " |

-continued

| $R^1$ | $R^2$ | $R^3$ | $R^4$ |
|---|---|---|---|
| " | " | 4-(N(CH$_3$)$_2$)-phenyl | " |
| " | C(=O)—CH$_3$ | H | " |
| " | " | CH$_3$ | " |
| " | C(=O)—CH$_2$—CH$_3$ | CH$_3$ | " |
| " | C(=O)—CH$_3$ | H | CH$_3$ |
| " | " | CH$_3$ | " |
| " | " | " | CH$_2$CH$_3$ |
| " | OH | C(=O)—CH$_3$ | H |
| " | C(=O)—CH$_2$OH | H | H |
| " | " | CH$_3$ | H |
| " | C(=O)—CH$_2$Cl | H | H |
| " | " | CH$_3$ | H |
| CH$_3$ | OH | CF=CF$_2$ | H |
| " | " | 2-pyridyl | " |
| " | " | 3-pyridyl | " |
| " | " | 4-pyridyl | " |
| " | O—CH$_2$—CH=CH— | H | " |
| C$_2$H$_5$ | OH | C≡C—H | H |
| " | " | C≡C—CH$_2$—CH$_3$ | H |
| " | " | C≡C—(CH$_2$)—CH$_3$ | H |
| " | " | C≡C—Ph | " |
| " | " | C≡C—CF$_3$ | " |
| " | " | C≡C—CF$_2$—CF$_3$ | " |
| " | " | CH=CH$_2$ | " |
| " | " | CH=CH—CH$_3$ (Z) | " |
| " | " | CH$_2$—C(CH$_3$)=CH$_2$ | " |
| " | " | Ph | " |
| " | " | CF$_2$—CF$_3$ | " |
| " | " | CH$_2$—Ph | " |
| " | " | CH$_2$—CH$_2$—CO$_2$H | " |
| " | " | C≡C—SCH$_3$ | " |
| " | " | C≡C—SPh | " |
| " | " | CH=C=CH$_2$ | " |
| " | " | CH$_2$—C≡C—H | " |
| " | O—C(=O)—NH—CH$_2$ | CH$_2$ | " |
| " | C(=O)—CH$_3$ | H | " |
| " | " | CH$_3$ | " |

-continued

| R¹ | R² | R³ | R⁴ |
|---|---|---|---|
| " | C(=O)—CH₂—CH₃ | CH₃ | " |
| " | C(=O)—CH₃ | H | CH₃ |
| " | " | CH₃ | " |
| " | " | " | CH₂CH₃ |
| " | OH | C(=O)—CH₃ | H |
| C₂H₅ | C(=O)—CH₂OH | H | H |
| " | " | CH₃ | H |
| " | C(=O)—CH₂Cl | H | H |
| " | " | CH₃ | H |
| " | OH | CF=CF₂ | H |
| " | " | 2-pyridyl | " |
| " | " | 3-pyridyl | " |
| " | " | 4-pyridyl | " |
| " | " | H | " |
| " | " | CH₂—CN | " |
| " | O—CH₂—CH=CH— | | " |

(B) The products of formula:

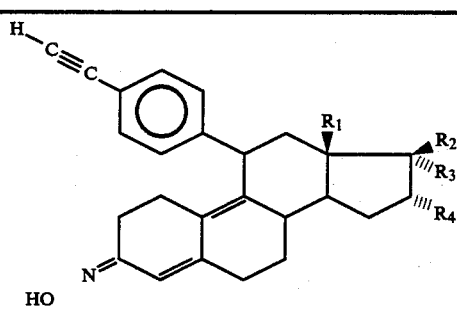

| R¹ | R² | R³ | R⁴ |
|---|---|---|---|
| CH₃ | OH | C≡C—H | H |
| " | " | C≡C—CH₂CH₃ | H |
| " | " | C≡C—(CH₂)₂CH₃ | H |
| " | " | C≡C—C(=CH₂)CH₃ | H |
| " | " | C≡C—Ph | " |
| " | " | C≡C—CF₃ | " |
| " | " | C≡C—CF₂CF₃ | " |
| " | " | CH≡CH₂ | " |
| " | " | CH₂—CH₃ | " |
| " | " | CH₃ | " |
| " | " | CH₂CH₂OH | " |
| " | " | CH₂CH₂CH₂OH | " |
| " | " | CH=CH—CH₃ (E) | " |
| " | " | CH=CH—CH₃ (Z) | " |
| " | " | CH₂—C(CH₃)=CH₂ | " |

-continued

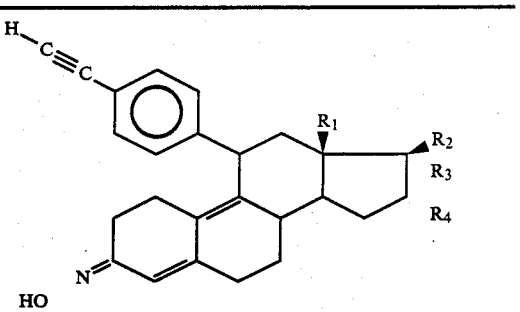

| R¹ | R² | R³ | R⁴ |
|---|---|---|---|
| " | " | Ph | " |
| " | " | CF₂CF₃ | " |
| " | " | CH₂Ph | " |
| " | " | CH₂CH₂—CO₂H | " |
| " | " | C≡C—S CH₃ | " |
| " | " | C≡C—SPh | " |
| " | " | CH=C=CH₂ | " |
| " | " | CH₂C≡C—H | " |
| " | " | (CH₂)₃CH₃ | " |
| " | C(=O)—CH₃ | H | " |
| " | " | CH₃ | " |
| " | C(=O)—CH₂—CH₃ | CH₃ | " |
| " | C(=O)—CH₃ | H | CH₃ |
| " | " | CH₃ | " |
| " | " | " | CH₂CH₃ |
| " | OH | C(=O)—CH₃ | H |
| " | C(=O)—CH₂OH | H | H |
| " | " | CH₃ | H |
| " | C(=O)—CH₂Cl | H | H |
| " | " | CH₃ | H |
| CH₃ | OH | CF=CF₂ | H |
| " | " | 2-pyridyl | " |
| " | " | 3-pyridyl | " |
| " | " | 4-pyridyl | " |
| " | " | H | " |
| " | " | CH₂—CN | " |
| " | O-CH₂—CH=CH— | | " |

(C) The products of formula:

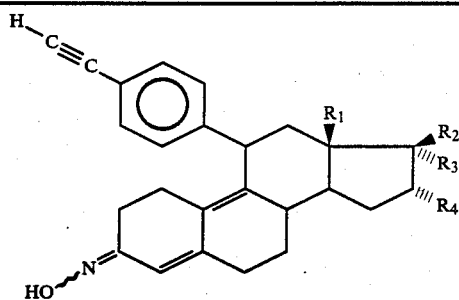

| R¹ | R² | R³ | R⁴ |
|---|---|---|---|
| CH₃ | OH | C≡C—H | H |
| " | " | C≡C—CH₂CH₃ | H |
| " | " | C≡C—(CH₂)₂CH₃ | H |
| " | " | C≡C—C(CH₃)=CH₂ | H |
| " | " | C≡C—Ph | " |
| " | " | C≡C—CF₃ | " |
| " | " | C≡C—CF₂CF₃ | " |
| " | " | CH=CH₂ | " |
| " | " | CH₂—CH₃ | " |
| " | " | CH₃ | " |
| " | " | CH₂CH₂OH | " |
| " | " | CH₂CH₂CH₂OH | " |
| " | " | CH=CH—CH₃ (E) | " |
| " | " | CH=CH—CH₃ (Z) | " |
| " | " | CH₂—C(CH₃)=CH₂ | " |
| " | " | Ph | " |
| " | " | CF₂CF₃ | " |
| " | " | CH₂Ph | " |
| " | " | CH₂CH₂—CO₂H | " |
| " | " | C≡C—S CH₃ | " |
| " | " | C≡C—SPh | " |
| " | " | CH=C=CH₂ | " |
| " | " | CH₂C≡C—H | " |
| " | " | (CH₂)₃CH₃ | " |
| " | C(=O)—CH₃ | H | " |
| " | " | CH₃ | " |
| " | C(=O)—CH₂—CH₃ | CH₃ | " |
| " | C(=O)—CH₃ | H | CH₃ |
| " | " | CH₃ | " |
| " | " | " | CH₂CH₃ |
| " | OH | C(=O)—CH₃ | H |
| " | C(=O)—CH₂OH | H | H |
| " | " | CH₃ | H |

| R¹ | R² | R³ | R⁴ |
|---|---|---|---|
| " | " | C(=O)—CH₂Cl | H |
|  |  |  | H |
| CH₃ | OH | CH₃ | H |
| " | " | CF=CF₂ | H |
| " | " | 2-pyridyl | " |
| " | " | 3-pyridyl | " |
| " | " | 4-pyridyl | " |
| " | " | H | " |
| " | " | CH₂—CN | " |
| " | O—CH₂—CH=CH— |  | " |

(D) The products of formula:

| R¹ | R² | R³ | R⁴ |
|---|---|---|---|
| CH₃ | OH | C≡C—H | H |
| " | " | C≡C—CH₂CH₃ | H |
| " | " | C≡C—(CH₂)₂CH₃ | H |
| " | " | C≡C—C(CH₃)=CH₂ | H |
| " | " | C≡C—Ph | " |
| " | " | C≡C—CF₃ | " |
| " | " | C≡C—CF₂CF₃ | " |
| " | " | CH=CH₂ | " |
| " | " | CH₂—CH₃ | " |
| " | " | CH₃ | " |
| " | " | CH₂CH₂OH | " |
| " | " | CH₂CH₂CH₂OH | " |
| " | " | CH=CH—CH₃ (E) | " |
| " | " | CH=CH—CH₃ (Z) | " |
| " | " | CH₂—C(CH₃)=CH₂ | " |
| " | " | Ph | " |
| " | " | CF₂CF₃ | " |
| " | " | CH₂Ph | " |
| " | " | CH₂CH₂—CO₂H | " |

-continued

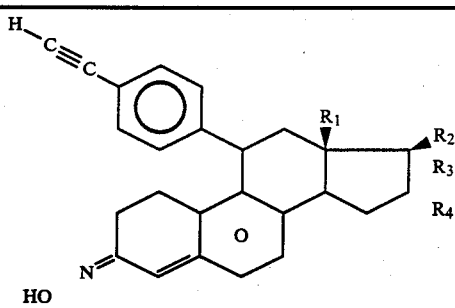

| R¹ | R² | R³ | R⁴ |
|---|---|---|---|
| " | " | C≡C—S CH₃ | " |
| " | " | C≡C—SPh | " |
| " | " | CH=C=CH₂ | " |
| " | " | CH₂C≡C—H | " |
| " | " | (CH₂)₃CH₃ | " |
| " | C(=O)—CH₃ | H | " |
| " | " | CH₃ | " |
| " | C(=O)—CH₂—CH₃ | CH₃ | " |
| " | C(=O)—CH₃ | H | CH₃ |
| " | " | CH₃ | " |
| " | " | " | CH₂CH₃ |
| " | OH | C(=O)—CH₃ | H |
| " | C(=O)—CH₂OH | H | H |
| " | " | CH₃ | H |
| " | C(=O)—CH₂Cl | H | H |
| " | " | CH₃ | H |
| CH₃ | OH | CF=CF₂ | H |
| " | " | 2-pyridyl | " |
| " | " | 3-pyridyl | " |
| " | " | 4-pyridyl | " |
| " | " | H | " |
| " | " | CH₂—CN | " |
| " | O-CH₂—CH=CH— | | " |

(E) The products of formula:

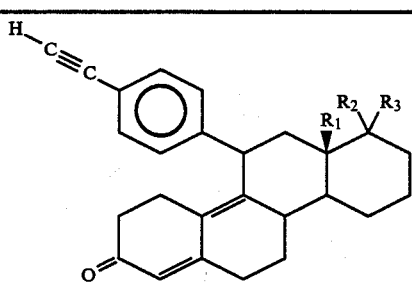

| R¹ | R² | R³ | R⁴ |
|---|---|---|---|
| CH₃ | OH | C≡C—H | H |

-continued

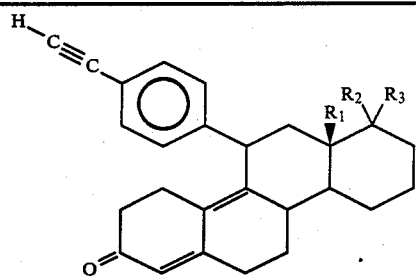

| R¹ | R² | R³ | R⁴ |
|---|---|---|---|
| " | " | C≡C—CH₂CH₃ | H |
| " | " | C≡C—(CH₂)₂CH₃ | H |
| " | " | C≡C—C(CH₃)=CH₂ | H |
| " | " | C≡C—Ph | " |
| " | " | C≡C—CF₃ | " |
| " | " | C≡C—CF₂CF₃ | " |
| " | " | CH=CH₂ | " |
| " | " | CH₂—CH₃ | " |
| " | " | CH₃ | " |
| " | " | CH₂CH₂OH | " |
| " | " | CH₂CH₂CH₂OH | " |
| " | " | CH=CH—CH₃ (E) | " |
| " | " | CH=CH—CH₃ (Z) | " |
| " | " | CH₂—C(CH₃)=CH₂ | " |
| " | " | Ph | " |
| " | " | CF₂CF₃ | " |
| " | " | CH₂Ph | " |
| " | " | CH₂CH₂—CO₂H | " |
| " | " | C≡C—S CH₃ | " |
| " | " | C≡C—SPh | " |
| " | " | CH=C=CH₂ | " |
| " | " | CH₂C≡C—H | " |
| " | " | (CH₂)₃CH₃ | " |
| " | C(=O)—CH₃ | H | " |
| " | " | CH₃ | " |
| " | C(=O)—CH₂—CH₃ | CH₃ | " |
| " | C(=O)—CH₃ | H | CH₃ |
| " | " | CH₃ | " |
| " | " | " | CH₂CH₃ |
| " | OH | C(=O)—CH₃ | H |
| " | C(=O)—CH₂OH | H | H |
| " | " | CH₃ | H |
| " | C(=O)—CH₂Cl | H | H |

-continued

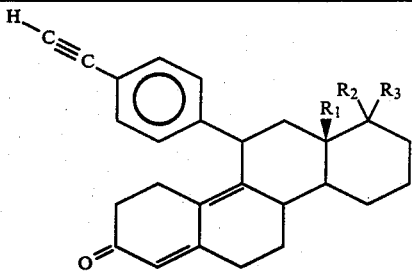

| R¹ | R² | R³ | R⁴ |
|---|---|---|---|
| " | " | CH₃ | H |
| CH₃ | OH | CF=CF₂ | H |
| " | " | 2-pyridyl | " |
| " | " | 3-pyridyl | " |
| " | " | 4-pyridyl | " |
| " | " | H | " |
| " | " | CH₂—CN | " |
| " | O—CH₂—CH=CH— | | " |

In the following examples there are described several preferred embodiments to illustrate the inventin. However, it should be understood that the invention is not intended to be limited to the specific embodiments.

EXAMPLE 1

17α-(1-propynyl)-11β-[4-(1-propynyl)-phenyl]-Δ$^{4,9}$-estradien-17β-ol-3-one

Step A: 1-(4-bromophenyl)-propyne

Under an inert atmosphere, 75 g of p-bromopropiophenone and 78.5 g of phosphorus pentachloride were mixed together and heated progressively to arrive at 100° C. in one hour and a strong evolution of hydrochloric acid was observed during about 20 minutes. The phosphorus trichloride formed was distilled off under reduced pressure, and after rectifying, 63 g of the still impure product sought was obtained. The latter was introduced into a mixture of 250 ml of ethanol and 65 g of potassium hydroxide in pellets and the mixture was heated to reflux which was maintained for 2 hours 30 minutes. Then the reaction mixture was poured into 1 liter of water and ice and after extraction with ether, washing with salted water, drying, concentrating to dryness by distillating under reduced pressure and rectifying, 24.2 g of 1-(4-bromophenyl)propyne with a boiling point at 0.1 mbar of 72° to 74° C. were obtained.

Step B:
3,3-dimethoxy-11β-[4-(propynyl)-phenyl]-17α-propynyl-Δ⁹-estraene-5α,17β-diol At 10° C. and under an inert atmosphere, 150 mg of CuCl were added to a solution of 1.49 g of 3,3-dimethoxy-17β-hydroxy-5α,10α-epoxy-17α-(1-propynyl)-Δ$^{9(11)}$-estraene in 15 ml of anhydrous tetrahydrofuran. Then to the green suspension, there were added 20 ml of 1-propenylphenyl magnesium

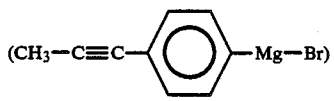

in solution in tetrahydrofuran titrating 0.75 M/l and the mixture was heated for 90 minutes at 20° C. 20 ml of a 10% solution of NH₄Cl and 50 ml of water were added with strong stirring in the presence of air

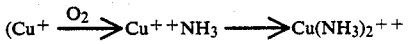

soluble and blue). Extraction was effected with ethyl acetate and the extracts were dried, filtered, and concentrated to dryness under reduced pressure. The residue was chromatographed over silica and eluted with a mixture of methylene chloride and acetone (95-5) to obtain 1.52 g of 3,3-dimethoxy-11β-[4-(propynyl)-phenyl]-17α-propynyl-Δ⁹-estraene-5α,17β-diol.

| IR Spectrum (chloroform) | |
|---|---|
| absorption at 3602 cm$^{-1}$ and 2250 cm$^{-1}$ | 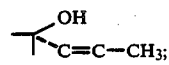 |
| 3470 cm$^{-1}$ | —OH; |
| 2220 cm$^{-1}$ | 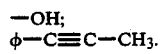 |
| NMR Spectrum (deuterochloroform) | |
| peak at 0.45 ppm: | hydrogens of the 18 Me |
| peaks at 1.06–1.89 ppm: | hydrogens of ≡C—CH₃ |
| peaks at 3.21–3.23 ppm: | hydrogens of the 2-OCH₃ |
| peaks at 4.24–4.33 ppm: | hydrogen at 11 |
| peak at 4.71 ppm: | hydrogen of OH |
| peaks at 7.08–7.17 ppm) | } aromatic hydrogens |
| peaks at 7.24–7.33 ppm | |

Step C:
17α-(1-propynyl)-11β-[4-(1-propynyl)-phenyl]-Δ$^{4,9}$-estradien-17β-ol-3-one 1 g of 3,3-dimethoxy-11β-[4-(propynyl)-phenyl]-17α-propynyl-Δ⁹-estraene-5α,17β-diol of Step B, 10 ml of ethanol, and 2 g of "cedex" resin previously washed with ethanol were mixed together and the reaction mixture was refluxed for 90 minutes, then filtered. The filtrate was concentrated to dryness by distilling under reduced pressure, and the residue was chromatographed over silica. Elution with a mixture of methylene chloride and ethyl acetate (97.5-2.5) yielded 803 mg of crude product which was then dissolved in 5 ml of ether, and 5 ml of isopropyl ether was added. Crystallization was initiated and then the ether was distilled off under reduced pressure until a volume of about 5 ml remained. After separating, washing with isopropyl ether and drying, 539 mg of 17α-(1-propynyl)-11β-[4-(1-propynyl)-phenyl]-Δ$^{4,9}$-estradien-17β-ol-3-one melting at 120°–130° C. and having a specific rotation $[α]_D^{20} = +147°$ (c=0.5%, CHCl₃) were obtained.

IR Spectrum (chloroform) absorption at 3603 cm$^{-1}$: OH; absorption at 2220 cm$^{-1}$ and 2250 cm$^{-1}$: C≡C; absorption at 1654 cm$^{-1}$ and 1600 cm$^{-1}$: C=O and C=C.

NMR Spectrum (deuterochloroform) peak at 0.5 ppm: hydrogens of the 18 Me; peaks at 1.92 and 2.07 ppm: hydrogens of ≡C—CH₃; peaks at 4.37–4.44 ppm: hydrogen at position 11; peak at 5.8 ppm: hydrogen at position 4; peaks at 7.09 and 7.311 ppm: 4H aromatics, quadruplet J=8 Hz.

| UV Spectrum (ethanol) | |
|---|---|
| λ max: 246 | ε = 22,000; |
| λmax: 255 | ε = 22,900; |
| λmax: 301 | ε = 18,100. |
| Circular dichroism (EtOH) | |

| | |
|---|---|
| λ = 250 nm | ΔΣ = −27.5 |
| λ = 256 nm | ΔΣ = −31.2 |
| λ = 301 nm | ΔΣ = +22.8 |
| λ = 356 nm | ΔΣ = −0.75 |

EXAMPLE 2

11β-(3-ethynylphenyl)-17α-(1-propynyl)-Δ$^{4,9}$-estradien-17β-ol-3-one

Step A: 1-bromo-3-ethynylbenzene 38 g of m-bromoacetophenone and 42 g of phosphorus pentachloride were allowed to react for 15 minutes and then were heated to 70° to 75° C. for 1 hour. The phosphorus oxychloride formed was distilled off under 100 mg of Hg and the remainder were distilled to dryness under reduced pressure to obtain 37 g of intermediate chlorated derivatives with a boiling point at 5 mm/Hg=90° to 100° C.

45 g of potassium hydroxide in pellets were introduced into 150 ml of alcohol with stirring for 30 minutes until completely dissolved at 30° C. 37 g of the intermediate product were added all at once, and the mixture was maintained at reflux for 2 hours. The reaction mixture was poured into 1 liter of iced water and was extracted with ether. The extracts were dried, and concentrated to dryness by distilling under reduced pressure. 200 ml of methylene chloride were added to the residue which was then treated with activated charcoal, stirred, dried, filtered, and the filtrate was concentrated to dryness by distilling under reduced pressure. After rectifying under 10.15 mm Hg, 9.5 g of 1-bromo-3-ethynylbenzene with a boiling point at 10-15 mm/Hg=80° to 85° C.

Step B: 3-(trimethylsilylethynyl)-bromobenzene

Under an inert atmosphere, 9.5 g of the compound of Step A were introduced into 100 g of tetrahydrofuran, and at 25° C.±3° C., over 15 minutes, 69 ml of a 0.8M solution of magnesium ethyl bromide were added, with stirring for 15 minutes at 25° C. Then, over 2 minutes and without cooling, 8 ml of trimethylsilyl chloride were added with stirring for 30 minutes at 25° C. The reaction mixture was poured into a 2M aqueous solution of NH4Cl and was extracted with ether, dried, filtered, and the filtrate was concentrated to dryness by distilling under reduced pressure then rectified to obtain 12.1 g of 3-(trimethylsilylethynyl)bromobenzene with a boiling point at 0.05 mm/Hg=78° to 84° C.

IR Spectrum (chloroform) absorption at 2160 cm$^{-1}$; C≡C; 1250 cm$^{-1}$, 874 cm$^{-1}$ and 845 cm$^{-1}$: Si-Me3 1590 cm$^{-1}$, 1581 cm$^{-1}$, 1520 cm$^{-1}$ and 1503 cm$^{-1}$: aromatic nucleus.

NMR Spectrum (deuterochloroform) peak at 0.23 ppm: hydrogens at ME3Si; peaks from 6.98 to 7.62 ppm: hydrogens of the aromatic nuclei.

Step C:
3,3-dimethoxy-11β-(3-trimethylsilylethynylphenyl)-17α-propynyl-Δ$^9$-estren-5α,17β-diol Under an inert atmosphere, 5 g of 3-(trimethylsilylethynyl) bromo-benzene were added to 100 ml of ether over about 5 minutes at −5° C. and then 12.5 ml of a 11.6M suspension of n-BuLi in hexane were added with stirring for 45 minutes at −2° C. followed by cooling to −7° C. Over 5 minutes, 1.9 g of CuI were added in small fractions with stirring for 30 minutes at −5° C., then over 5 minutes, a solution of 1.5 g of 3,3-dimethoxy-17α-(1-propynyl)-5α,10α-epoxy-Δ$^{9(11)}$-estrene-17β-ol in 15 ml of ether were added. The mixture was allowed to return to ambient temperature and after stirring for 1 hour, the reaction mixture was poured into 200 ml of 1M NH4C. 2.5 ml of concentrated ammonia were added with strong stirring in the presence of air

blue, soluble). After stirring for a further 15 minutes, extracting with ether, drying, concentrating to dryness by distilling under reduced pressure, and chromatographing the residue over silica and eluting with a mixture of methylene chloride, ethyl acetate and triethylamine (97-3-0.4), 720 mg of 3,3-dimethoxy-11β-(3-trimethylsilylethynylphenyl)-17α-propynyl-Δ$^9$-estren-5α,17β-diol with a specific rotation of $[α]_D^{20} = -74.5°$ (c=0.6% CHCl3) were obtained.

IR Spectrum (chloroform)

| absorption at 3473 cm$^{-1}$: | OH combined |
|---|---|
| 2156 cm$^{-1}$: | C≡C—Si—; |
| 1237 cm$^{-1}$ and 846 cm$^{-1}$: | SiMe3; |
| 1102 cm$^{-1}$ 1047 cm$^{-1}$: | ketal |
| 1596 cm$^{-1}$ 1573 cm$^{-1}$ and 1479 cm$^{-1}$: | aromatics |
| 3606 cm$^{-1}$ 2136 cm$^{-1}$ | ╱OH ╲C≡C—CH3 |

NMR Spectrum (deuterochloroform)

| peak at 0.25 ppm: | hydrogens of Si(CH3)3 |
|---|---|
| peak at 0.45 ppm: | hydrogens of 18 Me; |
| peak at 1.89 ppm: | hydrogens of the methyl of C≡C—CH3; |
| peaks at 4.25-4.73 ppm: | hydrogen at 11; |
| peaks at 7.11-7.37 ppm: | hydrogen of the aromatic nucleus. |

Step D:
11β-(3-ethynylphenyl)-17α-(1-propynyl)-Δ$^{4,9}$-estraene-17β-ol-3-one 680 mg of the product of Step C, 20 ml of methanol, and 0.7 ml of a 2N aqueous solution of sodium hydroxide were admixed with stirring for 30 minutes at 20° C. and 1 ml of a 2N aqueous solution of hydrochloric acid was added with stirring for 1 hour at ambient temperature. Then 1 ml of an M aqueous solution of CO3HK was added, and the mixture was concentrated under reduced pressure. Ethyl acetate was added to the residue, followed by washing with water, drying and concentrating to dryness by distilling under reduced pressure. The residue was chromatographed over silica and eluted with a mixture of methylene chloride and ethyl acetate (95-5) to obtain 383 mg of 11β-(3-ethynylphenyl)-17α-(1-propynyl)-Δ$^{4,9}$-estraen-17β-ol-3-one with a specific rotation of $[α]_D^{20} = +62°$ (c=0.5% chloroform).

IR Spectrum (chloroform)
absorption at 3600 cm$^{-1}$: OH;
absorption at 3304 cm$^{-1}$ and 2100 cm$^{-1}$: —C≡C—CH;
absorption at 2235 cm$^{-1}$: —C≡C—C;

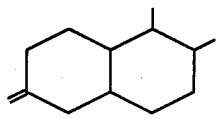

| | |
|---|---|
| | C = O  1675 cm$^{-1}$ |
| | C=C  1596 cm$^{-1}$ | absorption at 1576 cm$^{-1}$ and 1480 cm$^{-1}$: aromatics;
NMR Spectrum (deuterochloroform)

| peak at 0.53 ppm: | hydrogens of the 18 Me |
| peak at 1.93 ppm: | hydrogens of the methyl of C≡C—CH$_3$ |
| peak at 3.08 ppm: | hydrogen of H—C≡C—⟨ |
| peaks of 4.4 to 4.47 ppm: | hydrogen at 11 |
| peak at 5.82 ppm: | hydrogen at 4 |
| peaks of 7.2 to 7.36 ppm: | hydrogens of the aromatic nucleus. |

UV Spectrum (chloroform)

| max: 238 | $\epsilon = 18,300$; |
| max: 247 | $\epsilon = 16,100$; |
| max: 301 | $\epsilon = 19,800$. |

Circular dichroism

| 214 nm | $\Delta\epsilon = -6$ |
| 248 nm | $\Delta\epsilon = -4.4$ |
| 280 nm | $\Delta\epsilon = +9.7$ |
| 286 nm | $\Delta\epsilon = +12$ |
| 300 nm | $\Delta\epsilon = +14.5$ |
| 350 nm | $\Delta\epsilon = -1$ |

NMR Spectrum (deuterochloroform) peak at 0.53 ppm: hydrogens of the 18 Me; peak at 1.93 ppm: hydrogens of the methyl of C≡C—CH$_3$; peak at 3.08 ppm: hydrogen of

EXAMPLE 3

11β-(4-ethynylphenyl)-17α-(1-propynyl)-Δ$^{4,9}$-estradien-17β-ol-3-one

STEP A: p-bromophenyl acetylene

Stage 1: Preparation of intermediate chlorinated derivatives by the action of phosphorus pentachloride on p-bromoacetophenone.

A mixture of 95 g of p-bromoacetophenone and 107 g of phosphorus pentachloride was heated to 70° C., and after melting, a large evolution of hydrochloric acid was observed. After holding at 70° C. for 10 minutes, then distilling under reduced pressure, a first fraction of 10 g was obtained corresponding to the monochlorinated product,

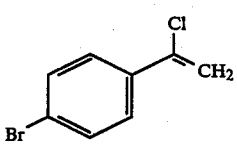

distilling at 95° C. at 5 mm/Hg, and a second fraction was obtained distilling at 100°–102° C. at 5 mm/Hg and corresponding to the chlorinated derivative

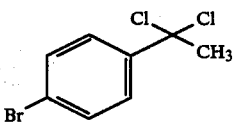

Because the two products lead, after treatment, to the same derivative, they were kept together for a total weight of 83.5 g (Mixture A).

Stage 2: Peparation of p-bromophenylacetylene by action of potassium hydroxide on the intermediate halogenated derivatives.

Mixture A was introduced into 430 g of a 25% solution of potassium hydroxide in ethanol and the mixture was refluxed for 3 hours, then cooled. The reaction mixture was poured into 2.5 l. of iced water, and was extracted with ether. The extracts were washed with water, dried and filtered and the filtrate was concentrated to dryness by distilling under reduced pressure, then rectified under reduced pressure to obtain 26.5 g of p-bromophenyl acetylene with a boiling point of 90° C. at 10 mm Hg.

STEP B: p-bromophenylethynyl trimethylsilane

Stage 1: Preparation of magnesium ethyl bromide.

Under an inert atmosphere, 8.5 g of magnesium turnings were introduced into 20 ml of ether, and a few drops of ethyl bromide were added. The mixture was heated to initiate the reaction and then 25 ml of ethyl bromide in 300 ml of ether were added over 1 hour while maintaining the reflux. Stirring was continued for 30 minutes after the end of the introduction and the mixture was allowed to rest. Titre: 0.7 mole/l.

Stage 2: Preparation of the silyl derivative

Dropwise over 30 minutes, 26.4 g of p-bromophenyl acetylene in solution in 100 ml of tetrahydrofuran were added to 215 ml of the magnesium compound solution prepared above and the reaction was lively and immediately was accompanied by an evolution of ethane and a rise in temperature. The temperature was brought back to 15°–20° C. and stirring was continued for 10 minutes. Over 5 minutes, 20 ml of chlorotrimethylsilane was added dropwise and after allowing the temperature to return to the ambient and stirring for 30 minutes, the reaction medium was diluted by the addition of 200 ml of a saturated aqueous solution of NH$_4$Cl, followed by decanting and extracting with tetrahydrofuran. The extracts were washed with salted water, dried and concentrated to dryness by distilling under reduced pressure. The oily residue was taken up in 150 ml of methanol and crystallization was initated. The crystals were separated, washed and dried to obtain 18.67 g of p-bromophenylethynyl trimethylsilane melting at about 65° C.

STEP C:
3,3-dimethoxy-17α-propynyl-11β-[4-[(trimethylsilyl)-ethynyl]phenyl]-Δ$^9$-estren-5α,17β-diol Stage 1: Preparation of the magnesium compound of the (p-bromophenylethynyl)-trimethylsilane Under an inert atmosphere, 2 g of magnesium turnings, 5 ml of anhydrous the trahydrofuran, and a few drops of brominated reagent were put together and reaction was initiated with a few drops of dibromoethane and heating. Then, over about 20 minutes while maintaining reflux, 18.6 g of (p-bromophenylethynyl)-trimethylsilane in 70 ml of tetrahydrofuran were introduced with stirring for a further 15 minutes at reflux and after allowing to rest, a magnesium compound titrating 1M/1 was obtained.

Stage 2: Condensation

At 0° C. and under an inert atmosphere, 1.86 g of 3,3-dimethoxy-5α,10α-epoxy-17β-(11-propynyl)-Δ$^{9(11)}$-estraene were introduced into 20 ml of anhydrous tetrahydrofuran and 100 mg of Cl₂Cu₂ were added followed by 30 ml of the magnesium compound solution obtained at stage 1 rapidly. After cooling to 0° C., stirring for 1 hour at 0° C. and allowing to return to +20 C. over 30 minutes, the reaction mixture was poured into a saturated aqueous solution of ammonium chloride. Extraction was done with ethyl acetate and the extracts were distilled under reduced pressure. The residue was chromatographed over silica and eluted with a mixture of methylene chloride and ethyl acetate (97-3) to obtain 2 g of 3,3-dimethoxy-17α-propynyl-11β-[4-[(trimethylsilyl)-ethynyl]-phenyl]-Δ⁹-estren-5α,17β-diol

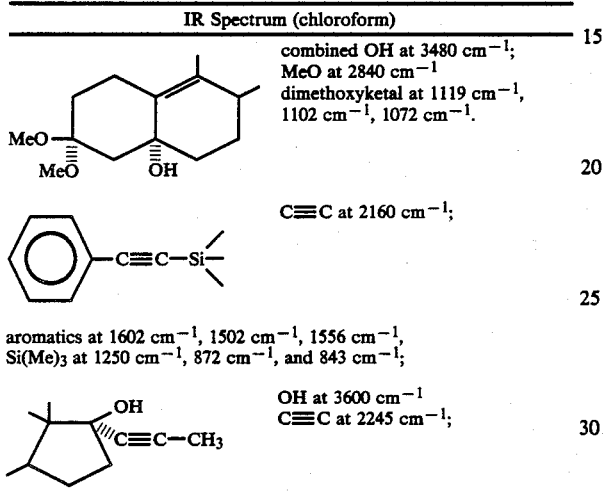

IR Spectrum (chloroform)

combined OH at 3480 cm⁻¹;
MeO at 2840 cm⁻¹
dimethoxyketal at 1119 cm⁻¹, 1102 cm⁻¹, 1072 cm⁻¹.

C≡C at 2160 cm⁻¹;

aromatics at 1602 cm⁻¹, 1502 cm⁻¹, 1556 cm⁻¹, Si(Me)₃ at 1250 cm⁻¹, 872 cm⁻¹, and 843 cm⁻¹;

OH at 3600 cm⁻¹
C≡C at 2245 cm⁻¹;

NMR Spectrum (deuterochloroform) peak at 0.24 ppm: hydrogens of SiMe₃; peak at 0.42 ppm: hydrogens of 18-Me; peak at 1.87 ppm: hydrogens of ≡C—Me; peaks at 3.20 and 3.40 ppm: hdyrogens of OMe; peak at 4.28 ppm: hydrogen at 11; peak at 4.70 ppm: hydrogen of OH; peaks from 7.15 to 7.37 ppm: aromatic hydrogens.

STEP D:
11β-(4-ethynylphenyl)-17α-(11-pyropynyl)-Δ⁴,⁹-estradien-17β-ol-3-one

Stage 1: Separating the silyl

Under an atmosphere of nitrogen, 1 g of the silyl derivative obtained at Step C were added to 95 ml of methanol and 5 ml of water and the mixture was stirred until dissolved. 1 ml of 28% (12N) ammonia was added, and the reaction mixture was refluxed with stirring for 2 hours. 0.2 ml of a 10N aqueous solution of sodium hydroxide was added with stirring for 15 minutes at reflux to obtain solution A.

Stage 2: Dehydration, deketalization

The temperature of solution A was allowed to return towards 40° C. and 15 ml of a 2N aqueous solution of hydrochloric acid were added with stirring for 15 minutes at 40° C. It was cooled, diluted with water, and extracted with ethyl acetate. The extracts were washed with sodium bicarbonate, then with water, dried, and the filtrate was concentrated to dryness by distilling under reduced pressure. 5 ml of ether were added to the residue, and after initiating, crystallization was allowed to take place for 16 hours. The crystals were separated, washed, dried to obtain 383 mg of 11β-(4-ethynylphenyl)-17α-(11-propynyl)-Δ⁴,⁹-estradien-17β-ol-3-one melting at 155° C. and having a specific rotation of [α]_D = +140.5° (c=0.5%, chloroform).

The mother liquors were chromatographed over silica and eluted with a mixture of benzene and ethyl acetate (8-2) to obtain 335 mg of the crude product which was crystallized from ether for another 208 mg of the said product melting at 155° C.

IR Spectrum (chloroform)

—OH at 3600 cm⁻¹
—C≡C—Me at 2240 cm⁻¹

—C≡C—H { ≡CH at 3305 cm⁻¹
          C≡C at 2105 cm⁻¹

C = 0 at 1657⁻¹
C = 0 at 1600⁻¹;

C φ C at 1590 cm⁻¹, 1505 cm⁻¹ and 835 cm⁻¹.

NMR Spectrum (deuterochloroform) peak at 0.5 ppm: hydrogen of the 18—Me; peak at 1.92 ppm: hydrogens of the ≡C—Me; peak at 3.06 ppm: hydrogens of ≡C—H; peaks from 4.41 to 4.48 ppm: hydrogens at 11; peak at 5.82 ppm: hydrogen at 4.

EXAMPLE 4
11β-(4-ethynylphenyl)-17α-allyl-Δ⁴,⁹-estradien-17β-ol-3-one

Step A:

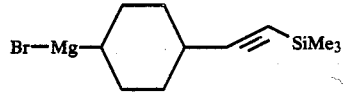

A few drops of mixture of 43.74 g of

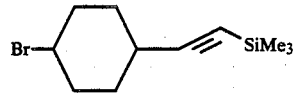

in 165 ml of tetrahydrofuran (mixture A) and under an inert atmosphere, were poured into 4.70 g of powdered magnesium in suspension in 12 ml of tetrahydrofuran and the reaction was initiated by gentle heating to 72° C. Addition was continued so as to maintain the temperature at 68°-71° C., followed by taking to reflux for 35 minutes to obtain a solution of the desired magnesium compound titrating 0.75 mole/l.

Step B:
3,3-ethylenedioxy-11β-[4-(2-trimethylsilylethynyl)-phenyl]-Δ⁹-estrene-5α-ol-17-one Under an atmosphere of nitrogen, 22.8 g of 3,3-ethylendioxy-5α,10α-epoxy-Δ⁹-estrene-17-one were introduced into 276 ml of tetrahydrofuran and the mixture was stirred until dissolved. Then, the temperature was brought to 0° C., and 1.38 g of CuCl were added. After stirring to dissolve this, 182 ml of a solution of Step A titrating 0.75 mole/l were poured in rapidly.

The temperature was allowed to drop to 0° C. with stirring for 1 hour at this temperature, after which it was allowed to rise to 20° C. over 30 minutes. 1400 ml of a saturated solution of NH₄Cl were added, followed by extracting with ethyl acetate. The extracts were washed with a saturated aqueous solution of sodium chloride, dried, filtered, and the filtrate was concentrated to dryness by distilling under reduced pressure. The residue was chromatographed under pressure and elution with a mixture of methylene chloride and ethyl acetate (9-1) yielded 5.9 g of 3,3-ethylenedioxy-11β-[4-(2-trimethylsilylethynyl)-phenyl]-Δ$^9$-estrene-5α,ol-17-one melting at 182° C.

IR Spectrum (chloroform) OH at 3510 cm$^{-1}$; C≡C strong at 2155 cm$^{-1}$; aromatics, 1602-1555-1500 cm$^{-1}$; 17-ketone at 1732 cm$^{-1}$; SiMe$_3$ probable.

| NMR Spectrum (deuterochloroform) | |
| --- | --- |
| peak at 0.24 ppm: | hydrogens of Me—Si—Me |
| peak at 0.47 ppm: | hydrogen of 17-Me |
| peak at 3.99 ppm: | hydrogens of 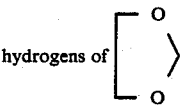 |
| peaks from 4.29 to 4.38 ppm: | hydrogens at 11 |
| peak at 4.41 ppm: | hydrogen of OH at 5 |
| peaks from 7.14 to 7.23 ppm peaks from 7.37 to 7.46 ppm | hydrogens of the aromatic nucleus. |

PREPARATION

Step C:
3,3-ethylenedioxy-11β-[4-(2-trimethylsilylethynyl)-phenyl]-17α-allyl-Δ$^9$-estrene-5α,17β-diol All of the magnesium compound prepared starting with 43 mmoles of allyl bromide or about 26 mmoles of allyl Mg-Br was placed in a flask and 3.01 g of 3,3-ethylenedioxy-11β-[4-(2-trimethylsilylethynyl)-phenyl]-Δ$^9$-estrene-5α-ol-17-one in solution in 32 ml of tetrahydrofuran were added dropwise over 7 minutes while stirring was continued for 1 hour at 20° C. and then 62 ml of a saturated aqueous solution of NH$_4$Cl were added, followed by extraction with ether. The extracts were washed with a saturated aqueous solution of sodium chloride, then dried and filtered, and the filtrate was concentrated to drynnes by distilling under reduced pressure. The residue was chromatographed over silica and elution with a mixture of methylene chloride and ethyl acetate (95-5), then with a mixture of methylene chloride and ethyl acetate (85-15) yielded 2.37 g of 3,3-ethylenedioxy-11β-[4-(2-trimethylsilylethynyl)-phenyl]-17α-allyl-Δ$^9$-estrene-5α,17β-diol melting at 192°-193° C.

IR Spectrum

Combined OH at 3505 cm$^{-1}$; ketal;

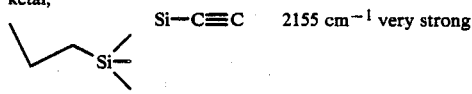 Si—C≡C  2155 cm$^{-1}$ very strong

SiMe  1250 cm$^{-1}$, 844 cm$^{-1}$, 834 cm$^{-1}$;

allyl    3077 cm$^{-1}$

| | |
| --- | --- |
| C=C deformation | 1635 cm$^{-1}$ 1000 cm$^{-1}$ shoulder. |

| NMR Spectrum (deuterochloroform) | |
| --- | --- |
| peak at 0.24 ppm: | hydrogens of Me—Si—Me |
| peak at 0.49 ppm: | hydrogens at 18 |
| peak at 3.98 ppm: | hydrogens of  |
| peaks from 4.28 to 4.34 ppm: | hydrogens at 11 |
| peak at 4.41 ppm: | hydrogen of OH at 5 |
| peaks at 5.05 to 5.24 ppm: | hydrogens of —CH=CH$_2$ |
| peaks at 5.83 to 6.22 ppm: | hydrogens of —CH=CH$_2$ |
| peaks at 7.11 to 7.21 ppm and peaks at 7.34 to 7.44 ppm | hydrogens of the aromatic nucleus |

Step D:
11β-(4-ethynylphenyl)-17α-allyl-Δ$^{4,9}$-estradiene-17β-ol-3-one

1st Stage: Separation of the silyl.

2.14 g of 3,3-ethylenedioxy-11β-[4-(2-trimethylsilylethynyl)-phenyl]-17α-allyl-Δ$^9$-estraene-5α,17β-diol were introduced into 200 ml of a methanol-water mixture (95-5) and the mixture was heated to 40° C. with stirring until solution was complete. Then 2.17 ml of NH$_4$OH (approx. 12N) were added, and the mixture was refluxed for 2 hours and 15 minutes. 0.78 ml of a 5N aqueous solution of sodium hydroxide were added with stirring for a further 15 minutes at refluxed then the temperature was allowed to cool to 38° C. To the reaction mixture at 38° C., 33 ml of a 2N aqueous solution of hydrochloric acid were added with stirring for 15 minutes at 20° C. The mixture was diluted with 200 ml of slightly salted water and extracted with ethyl acetate. The extracts were washed with a saturated aqueous solution of sodium chloride, dried, and the filtrate was concentrated to dryness by distilling under reduced pressure. The residue was chromatographed over silica and eluted with a mixture of methylene chloride and ethyl acetate (95-5) to obtain 1.35 g of 11β-(4-ethynylphenyl)-17α-allyl-Δ$^{4,9}$-estradiene-17β-ol-3-one melting at 116° C.

IR Spectrum

OH complex, 3620 cm$^{-1}$, 3600 cm$^{-1}$, 3560 cm$^{-1}$.

—C≡CH

| ≡C—H | 3305 cm$^{-1}$ |
| --- | --- |
| C≡C | 2108 cm$^{-1}$ |

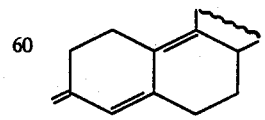

allyl group

| C=O | 1655 cm$^{-1}$ |
| --- | --- |
| C=C | 1603 cm$^{-1}$ |

| =C—H | 3080 cm$^{-1}$ |
| --- | --- |
| C=C | 1440 cm$^{-1}$ shoulder |
| deformation | 998 cm$^{-1}$ |
| deformation | 919 cm$^{-1}$ |

| | |
|---|---|
| aromatic | 1593 cm$^{-1}$ shoulder |
| nucleus | 1558 cm$^{-1}$ |
| | 1503 cm$^{-1}$ |

NMR Spectrum (deuterochloroform)

| | |
|---|---|
| peak at 0.55: | hydrogens of 18-Me |
| peak at 3.07 ppm: | hydrogens of H—C≡C— |
| peaks at 4.41 to 4.48 ppm: | hydrogens at 11 |
| peaks at 5.12 to 5.31 ppm: | hydrogen of —CH= CH$_2$ |
| peak at 5.81 ppm: | hydrogen at 4 |
| peaks from 5.83 to 6.22 ppm: | hydrogens at —(CH) =CH$_2$ |
| peaks at 7.11 to 7.21 ppm and peaks at 7.35 to 7.49 ppm | hydrogens of the aromatic nucleus |

EXAMPLE 5

17α-(chloroethynyl)-11β-(4-ethynylphenyl)-Δ$^{4,9}$-estradien-17β-ol-3-one

Step A:
3,3-ethylenedioxy-17α-chloroethynyl-11β-[4-[(trimethylsilyl)-ethynyl]-phenyl]-Δ$^9$-estrene-5α,17β-diol Into 10 ml of 1.6M n-butyllithium in hexane, there were added slowly at −5° C. 25 ml of ether then, dropwise, 0.67 ml of cis dichloroethylene in solution in 5 ml of ether with stirring of the suspension obtained for 10 minutes. 1.01 g of 3,3-ethylenedioxy-11β-[4-(2-trimethylsilylethynyl)-phenyl]-Δ$^9$-estrene-5α-ol-17-one in solution in 5 ml of tetrahydrofuran were added rapidly and then the temperature was allowed to return to 20° C. with stirring for 30 minutes. The reaction mixture was poured into an aqueous solution of NH$_4$Cl, and extracted with ether. The extracts were dried, filtered and the filtrate was concentrated to dryness by distilling under reduced pressure. The residue was chromatographed over silica and eluted with a mixture of methylene chloride and ethyl acetate (95-5) to obtain after crystallizing from isopropyl ether, 884 mg of 3,3-ethylenedioxy-17α-chloroethynyl-11β-[4-[(trimethylsilyl)-ethynyl]-phenyl]-Δ$^9$-estrene-5α,17β-diol.

IR Spectrum (chloroform)
Presence of

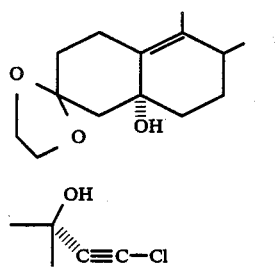

| | |
|---|---|
| | combined OH at 3500 cm$^{-1}$ |
| | OH 3600 cm$^{-1}$ |
| | C≡C 2220 cm$^{-1}$ |

| | C≡C 2157 cm$^{-1}$ |
|---|---|
| aromatics | 1602 cm$^{-1}$ |
| | 1555 cm$^{-1}$ |
| | 1500 cm$^{-1}$ |
| SiMe$_3$ | 1250 cm$^{-1}$ |
| | 867 cm$^{-1}$ |
| | 845 cm$^{-1}$ |

NMR Spectrum (deuterochloroform)

| | |
|---|---|
| peak at 0.25 ppm: | hydrogens of Me$_3$Si— |
| peak at 0.45 ppm: | hydrogens of the 18-Me |
| peaks at 3.74 to 4.44 ppm: | hydrogens of the OH |
| peak at 3.97 ppm: | hydrogens of $\begin{bmatrix} O \\ \phantom{x}\diagdown\!\!\!\diagup \\ O \end{bmatrix}$ |
| peaks at 4.3 to 4.37 ppm: | hydrogen at 11 |
| peaks at 7.17 to 7.2 ppm peaks at 7.3–7.43 ppm | hydrogens of the aromatic nucleus |

Step B:
17α-(chloroethynyl)-11β-(4-ethynylphenyl)-Δ$^{4,9}$-estradiene-17β-ol-3-one 3 ml of an N aqueous solution of sodium hydroxide were added to a solution of 860 mg of 3,3-ethylenedioxy-17α-chloroethynyl-11β-[4-(trimethylsilylethynyl)-phenyl]-Δ$^9$-estrene-5α,17β-diol of Step A in 30 ml of methanol with stirring for 20 minutes at 50° C., then for 1 hour at 20° C. 7 ml of an N aqueous solution of hydrochloric acid and 30 ml of methanol were added, and after standing at 20° C. for 30 minutes, the volume of solvent was reduced by distilling under reduced pressure. Ether was added and then the reaction mixture was poured into a saturated aqueous solution of sodium chloride and extracted with ether. The extracts were dried and filtered, and the filtrate was concentrated to dryness by distilling under reduced pressure. The residue was chromatographed over silica, eluted with a mixture of methylene chloride and ethyl acetate (95-5), followed by triturating in a mixture of ethanol and water and drying to obtain 450 mg of 17α-(chloroethynyl)-11β-(4-ethynylphenyl)-Δ$^{4,9}$-estradiene-17β-ol-3-one.

| IR Spectrum (chloroform) | |
|---|---|
| Absence of ketal | |
| Presence of OH | 3600 cm$^{-1}$ |
| C≡C—Cl | 2212 cm$^{-1}$ (C≡C) |
| C≡C—H | 3302 cm$^{-1}$ (≡C-H) |
| | 2100 cm$^{-1}$ (C≡C—) |
| dienone | 1657 cm$^{-1}$ (C=O) |
| | 1602 cm$^{-1}$ (C=C) |
| aromatic | 1555 cm$^{-1}$ |
| | 1503 cm$^{-1}$ |

NMR Spectrum (deuterochloroform)

| | |
|---|---|
| peak at 0.5 ppm | : hydrogens of 18-Me |
| peak at 3.05 ppm | : hydrogens of the H—C≡C— |

| -continued | |
|---|---|
| peak at 4.44 ppm | : hydrogens at 11 |
| peak at 5.8 ppm | : hydrogens at 4 |
| peaks at 7.11 to 7.21 ppm | } hydrogens of the aromatic nucleus |
| peaks at 7.38 to 7.48 ppm | |

EXAMPLE 6

17α-(chloroethynyl)-11β-(4-ethynylphenyl)-13α-Δ$^{4,9}$-estradien-17α-ol-3-one

Step A: 3,3-ethylenedioxy-11β-[4-[trimethylsilylethynyl]-phenyl]-13α-Δ$^9$-estren-5α-ol-17-one A solution of 3.7 g of 3,3-ethylenedioxy-11β-[4-(2-trimethylsilylethynyl)-phenyl]-Δ$^9$-estrene-5α-ol-17-one in 650 ml of dioxane was irradiated for 3 hours with a plunging mercury vapour lamp (Hanan TQ150) while the temperature of the solution was maintained at 22°–24° C. After concentrating to dryness by distilling under reduced pressure, and chromatographing the residue over silica and eluting with a mixture of hexane and ethyl acetate (4–6) with 0.1% of triethylamine, 1.6 g of 3,3-ethylene-dioxy-11β-[4-[trimethylsilylethynyl]-phenyl]-13α-Δ$^9$-estren-5α-ol-17-one melting at 182° C. were obtained.

IR Spectrum (chloroform)
Presence of

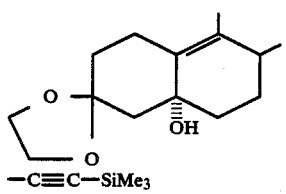

—C≡C—SiMe$_3$

| | | |
|---|---|---|
| | combined OH at 3508 cm$^{-1}$ | |
| | C≡C | 2155 cm$^{-1}$ |
| | SiMe$_3$ | 1250 cm$^{-1}$ |
| | | 864 cm$^{-1}$ |
| | | 844 cm$^{-1}$ |
| 17-keto | | 1730 cm$^{-1}$ |

NMR Spectrum (deuterochloroform)

| peak at 1.11 ppm | hydrogens of 18-Me |
|---|---|
| peak at 3.94 ppm | hydrogens of 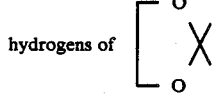 |
| peak at 4.33 popm | hydrogens of the hydroxyl at 5 |
| peaks at 7.03 to 7.12 ppm | } hydrogens of the aromatic nucleus |
| peaks at 7.33 to 7.43 ppm | |

Step B: Isomer A and Isomer B of 17-chloroethynyl-11β-[4-(trimethylsilylethynyl)-phenyl]-13α-Δ$^{4,9}$-estradien-17β-ol-3-one 10 ml of a suspension of n-BuLi in hexane titrating 1.6M were stirred under an inert atmosphere at 5° C. and 25 ml of ether were added slowly. Then 0.67 ml of cis dichloroethylene were added dropwise to obtain a suspension which was stirred for a further 10 minutes. 950 mg of 3,3-ethylenedioxy-11β-[4-(trimethylsilylethynyl)-phenyl]-13α-Δ$^9$-estren-5α-ol-17-one were added with stirring for 30 minutes and then the reaction mixture was poured into an aqueous solution of NH$_4$Cl and extracted with ether. The extracts were dried and filtered and the filtrate was concentrated to dryness by distilling under reduced pressure. The residue was chromatographed over silica and eluted with a mixture of methylene chloride and ethyl acetate (9-1) with 0.2% of triethylamine to obtain 115 mg of the isomer A of 17-chloroethynyl-11β-[4-(trimethylsilylethynyl)-phenyl]-13α-Δ$^{4,9}$-estradien-17β-ol-3-one and 235 mg of the isomer B.

| IR Spectrum of isomer A (chloroform) | |
|---|---|
| OH | 3600 cm$^{-1}$ |
| C≡C of C≡C—Cl | 2212 cm$^{-1}$ |
| C conjugated \| O | 1654 cm$^{-1}$ 1604 cm$^{-1}$ |
| | 2155 cm$^{-1}$ |
| C≡C of 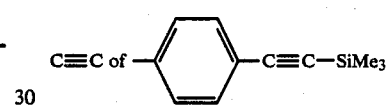 —C≡C—SiMe$_3$ | |
| aromatic | 1604 cm$^{-1}$ 1504 cm$^{-1}$ |
| SiMe$_3$ | 1250 cm$^{-1}$ 864 cm$^{-1}$ 845 cm$^{-1}$ |

| IR Spectrum of isomer B (chloroform) | |
|---|---|
| OH | 3601 cm$^{-1}$ |
| C≡C of C≡C—Cl | 2250 cm$^{-1}$ |
| C conjugated \|\| O | 1653 cm$^{-1}$ 1621 cm$^{-1}$ |
| | 2156 cm$^{-1}$ |
| C≡C of  —C≡C—SiMe$_3$ | |
| aromatic | 1605 cm$^{-1}$ 1503 cm$^{-1}$ |

Step C: Isomer A of 17-chloroethynyl-11β-(4-ethynylphenyl)-13α-Δ$^{4,9}$-estradien-17-ol-3-one Under an inert atmosphere 0.4 ml of an N aqueous solution of sodium hydroxide were added to 100 mg of a solution of isomer A of 17-chloroethynyl-11β-[4-(trimethylsilylethynyl)-phenyl]-13α-Δ$^{4,9}$-estradien-17-ol-3-one in methanol and after standing at 20° C. for 40 minutes, 1 ml of an N aqueous solution of hydrochloric acid was added. Some of the solvent was evaporated off and ether was added to the remainder which was then washed with a solution of sodium bicarbonate, dried, filtered, then concentrated to dryness by distilling under reduced pressure. The residue was triturated in isopropyl ether to obtain 55 mg of 17-chloroethynyl-11β-(4-ethynylphenyl)-13α-Δ$^{4,9}$-estradien-17-ol-3-one of which the configuration at 17 had not been determined. According to the literature (Steroids 44, p. 349), it should be 17β-OH, because of coming from the minority product at the time of the substitution at 17.

| UV Spectrum (ethanol) | | |
|---|---|---|
| max. 241 nm | $E_1^1 = 591$ | $\epsilon = 25,500$; |
| max. 251 nm | $E_1^1 = 569$ | $\epsilon = 24,500$; |
| infl. 276 nm | $E_1^1 = 207$; | |
| infl. 285 nm | $E_1^1 = 304$; | |
| max. 306 nm | $E_1^1 = 492$ | $\epsilon = 21,200$. |
| NMR Spectrum (deuterochloroform) | | |
| peak at 1.18 ppm | : | hydrogens of 18-Me |
| peak at 3.05 ppm | : | hydrogens of the H-C|C— |
| peak from 3.75 to 3.97 ppm | : | hydrogens at 11 |
| peak at 5.71 ppm | : | hydrogens at 4 |
| peaks at 7.08–7.17 ppm | } | hydrogens of the aromatic nucleus |
| peaks at 7.4–7.5 ppm | | |

Step D: Isomer B of 17-chloroethynyl-11β-(4-ethynylphenyl)-13α-Δ$^{4,9}$-estradien-17-ol-3-one 225 mg of isomer B of 17-chloroethynyl-11β-[4-[(trimethylsilyl)-ethynyl]-phenyl]-13α-Δ$^{4,9}$-estradien-17-ol-3-one were dissolved in 10 ml of methanol and nitrogen was bubbled in 1 ml of an N aqueous solution of sodium hydroxide was added, with stirring for 30 minutes under nitrogen at 20° C. 3 ml of N aqueous solution of hydrochloric acid were added and some of the solvent was evaporated under reduced pressure. Salted water was added, followed by extracting with ether. The extracts were dried and filtered and the filtrate was concentrated to dryness by distilling under reduced pressure. The residue was chromatographed over silica and eluted with a mixture of methylene chloride and ethyl acetate (9-1) to obtain 166 mg of 17-chloroethynyl-11β-(4-ethylphenyl)-13α-Δ$^{4,9}$-estradien-17-ol-3-one. The configuration at 17 of this product had not been demonstrated but based on the data in the literature (Steroids 44, page 349), it should be the 17α-OH isomer.

| IR Spectrum (Chloroform) | |
|---|---|
| OH | 3601 cm$^{-1}$ |
| C≡C of C≡C—Cl | 2215 cm$^{-1}$ |
| ≡C—H | 3302 cm$^{-1}$ |
| C≡C of C≡C—H | 2100 cm$^{-1}$ |
| C conjugated ‖ O | 1653 cm$^{-1}$ |
| C=C | 1621 cm$^{-1}$ |
| aromatic | 1606 cm$^{-1}$ |
| | 1504 cm$^{-1}$ |
| | 1557 cm$^{-1}$ |
| UV Spectrum (ethanol) | |
| max. 241 nm $E_1^1 = 552$ | $\epsilon = 23,800$ |
| max. 250 nm $E_1^1 = 526$ | $\epsilon = 22,700$ |
| infl. 277 nm $E_1^1 = 203$; | |
| infl. 282 nm $E_1^1 = 258$; | |
| infl. 285 nm $E_1^1 = 297$; | |
| max. 305 nm $E_1^1 = 466$ | $\epsilon = 20,100$ |
| NMR Spectrum (deuterochloroform) | |
| pic at 1.12 ppm | hydrogens of 18-Me |
| peak at 3.07 ppm | hydrogens of H—C≡C— |
| peak from 3.8 to 4.01 ppm | hydrogens at 11 |
| peak at 5.75 ppm | hydrogens at 4 |
| peaks at 7.11–7.21 ppm } | hydrogens of the |
| peaks at 7.43–7.53 ppm | aromastic nucleus |

EXAMPLE 7

17α-chloroethynyl-11β-[4-[(trimethylsilyl)-ethynyl]-phenyl]-Δ$^{4,9}$-estradien-17β-ol-3-one 100 mg of 3,3-ethylenedioxy-17α-chloroethynyl-11β-[4-[(trimethylsilyl)-ethynyl]-phenyl]-Δ$^9$-estren-5α,17β-diol were dissolved in 3 ml of methanol and 0.51 ml of an N aqueous solution of hydrochloric acid were added. The mixture stood at 20° C. for 5 hours and then was concentrated to dryness by distilling under reduced pressure. Chloroform was added with stirring followed by washing with water, then with an M aqueous solution of potassium bicarbonate, drying, filtering and concentrating the filtrate to dryness under reduced pressure. The residue was chromatographed over silica and eluted with a mixture of methylene chloride and ethyl acetate (95-5) to obtain 53 mg of 17α-chloroethynyl-11β-[4-[(trimethylsilyl)-ethynyl]-phenyl]-Δ$^{4,9}$-estradien-17β-ol-3-one.

| IR Spectrum (chloroform) | | | |
|---|---|---|---|
| Presence of 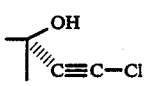 | | OH | 3600 cm$^{-1}$ |
| | | C≡C | 2212 cm$^{-1}$ |
| dioxan C ‖ O | | | 1657 cm$^{-1}$ |
|  | | C=C | 1601 cm$^{-1}$ |
| | | C≡C | 2156 cm$^{-1}$ |
| aromatic SiMe3 | | | 1503 cm$^{-1}$ |
| | | | 1251 cm$^{-1}$ |
| | | | 864 cm$^{-1}$ |
| | | | 844 cm$^{-1}$ |
| UV Spectrum (ethanol) | | | |
| infl. 235 nm $E_1^1 = 286$; | | | |
| infl. 245 nm $E_1^1 = 474$; | | | |
| max. 255 nm $E_1^1 = 627$ | | $\epsilon = 31,500$; | |
| max. 264 nm $E_1^1 = 580$ | | $\epsilon = 29,200$; | |
| infl. 280 nm $E_1^1 = 303$; | | | |
| max. 300 nm $E_1^1 = 427$ | | $\epsilon = 21,500$. | |
| NMR Spectrum (deuterochloroform) | | | |
| peak at 0.23 ppm | | hydrogens of the Me3Si | |
| peak at 0.48 ppm | | hydrogens of 18-Me | |
| peak at 4.44 ppm | | hydrogens of 11 | |
| peak at 5.83 ppm | | hydrogens at 4 | |
| peaks at 7.1–7.2 ppm } | | hydrogens of the | |
| peaks at 7.39–7.49 ppm | | aromatic nucleus | |

EXAMPLE 8

17α-chloroethynyl-9α,10α-epoxy-11β-(4-ethynylphenyl)-17-Δ$^4$-estraen-17β-ol-3-one To a solution of 215 mg of 17α-(chloroethynyl)-11β-(4-ethynylphenyl)-Δ$^{4,9}$-estradien-17β-ol-3-one in methylene chloride, 120 mmg of metachloroperbenzoic acid were added in several fractions with stirring for 1 hour at 20° C. After washing with an M solution of poassium bicarbonate, drying, filtering and concentrating to dryness by distilling under reduced pressure, the residue was chromatographed over silica and eluted with a mixture of methylene chloride and ethyl acetate (95-5) to obtain 165 mg of 17α-chloroethynyl-9α,10α-epoxy-11β-(4-ethynylphenyl)-17-Δ⁴-estraen-17β-ol-3-one.

| IR-Spectrum (chloroform) | |
|---|---|
| OH | 3600 cm$^{-1}$ |
| C≡C—Cl    C≡C | 2222 cm$^{-1}$ |
| —C≡C—H    C≡CH | 3303 cm$^{-1}$ |
| C≡C | 2120 cm$^{-1}$ |
| C=O | 1608 cm$^{-1}$ |
| Δ₄ C=C | 1623 cm$^{-1}$ |
| aromatics | 1608 cm$^{-1}$ |
| | 1557 cm$^{-1}$ |
| | 1505 cm$^{-1}$ |
| strong band at | 908 cm$^{-1}$, typical of |

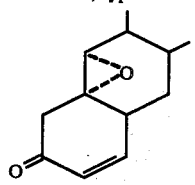

| UV Spectrum (ethanol) | | |
|---|---|---|
| infl. 240 nm $E_1^1$ = 670 | | |
| max. 244 nm $E_1^1$ = 733 | $\epsilon$ = 32,800; | |
| max. 254 nm $E_1^1$ = 636 | $\epsilon$ = 28,400; | |
| infl. 272 nm $E_1^1$ = 42 | | |
| infl. 280 nm $E_1^1$ = 16. | | |

NMR-Spectrum (deuterochloroform)

| | |
|---|---|
| peak at 0.46 ppm | hydrogens of 18-Me |
| peak at 3.08 ppm | hydrogens of H—C≡C— |
| peaks at 3.23–3.30 ppm | hydrogens at 11 |
| peak at 6.15 ppm | hydrogens at 4 |
| peaks at 7.19–7.29 ppm | } hydrogens of the |
| peaks at 7.45–7.55 ppm | aromatic nucleus |

EXAMPLE 9

17-acetate of 11β-(4-ethynylphenyl)-17α-(2-propenyl)-Δ¹,³,⁵(¹⁰)-estratrien-3,17β-diol and 11β-(4-ethynylphenyl)-17α-(2-propenyl)-Δ¹,³,⁵(¹⁰)-estra-trien-3,17β-diol 0.45 ml of acetic anhydride, and 0.25 ml of acetyl bromide were added at 0° C. to a solution of 500 mg of 11β-(4-ethynylphenyl)-17α-allyl-Δ⁴,⁹-estradien-17β-ol-3-one in 3 ml of methylene chloride, and the resulting mixture was stirred for 1 hour at 0° C. The reaction mixture was poured into 5 ml of M aqueous solution of potassium bicarbonate and was extracted with methylene chloride. The extracts were dried and filtrate was concentrated to dryness by distillation under reduced pressure. The residue was dissolved in 20 ml of methanol, degassed by bubbling nitrogen and 2 ml of 32% solution of sodium hydroxide were added. After stirring for 2 hours at 20° C. under an inert atmosphere, the reaction mixture was poured into a saturated aqueous solution of sodium chloride to which was added 15 ml of a 2N aqueous solution of hydrochloric acid. The mixture was extracted with chloroform and the extracts were dried and filtered. The filtrate was concentrated to dryness by distillation under reduced pressure and the residue was chromatographed over silica. Elution with a mixture of methylene chloride and ethyl acetate (95-5) yielded 231 mg of 17-acetate of 11β-(4-ethynylphenyl)-17α-(2-propenyl)-Δ¹,³,⁵(¹⁰)-estra-trien-3,17β-diol and 68 mg of 11β-(4-ethynylphenyl)-17α-(2-propenyl)-Δ¹,³,⁵(¹⁰)-estra-trien-3,17β-diol

| Physical characteristics of the acetate: | |
|---|---|
| IR Spectrum (chloroform) | |
| OH phenolic | 3599 cm$^{-1}$ |
| C≡C—H | 3302 cm$^{-1}$ |
| C≡C conjugated | 2100 cm$^{-1}$ |
| C=O acetate | 1724 cm$^{-1}$ |
| Me | 1368 cm$^{-1}$ |
| C—O—C | 1245 cm$^{-1}$ |
| Allyl =C—H | 3080 cm$^{-1}$ |
| C=C | 1640 cm$^{-1}$ |
| def. | 998 cm$^{-1}$ |
| | 920 cm$^{-1}$ |

| UV Spectrum (ethanol) | |
|---|---|
| infl. 240 nm $E_1^1$ = 401; | |
| max. 245 nm $E_1^1$ = 455 | $\epsilon$ = 20700; |
| max. 256 nm $E_1^1$ = 409 | $\epsilon$ = 18600; |
| max. 277 nm $E_1^1$ = 66 | $\epsilon$ = 3000; |
| max. 283 nm $E_1^1$ = 68 | $\epsilon$ = 3100; |
| max. 288 nm $E_1^1$ = 60 | $\epsilon$ = 2700; |
| infl. 309 nm $E_1^1$ = 15; | |
| infl. 323 nm $E_1^1$ = 12. | |

NMR Spectrum (deuterochloroform)

| | |
|---|---|
| peak at 0.36 ppm | hydrogens of 18-Me |
| peak at 1.92 ppm | hydrogens of O—C(=O)—CH₃ |
| peak at 2.97 ppm | hydrogens of H—C≡C— |
| peak at 4.03 ppm | hydrogens at 11 |
| peaks from 5.0 to 5.12 ppm | hydrogens of =CH₂ (vinyl) |
| peaks from 5.55 to 6.11 ppm | hydrogens of —CH= (vinyl) |
| peaks at 6.37–6.49 ppm | hydrogens at 2 |
| peaks at 6.63–6.65 ppm | hydrogens at 4 |
| peaks at 6.77–6.87 ppm | hydrogens at 1 |
| peaks at 7.04–7.13 ppm | } hydrogens of the |
| peaks at 7.21–7.3 ppm | aromatic nucleus. |

Physical characteristics of the alcohol.

| IR Spectrum (nujol) | |
|---|---|
| general absorption NH/OH region | |
| C≡C—H | 3308 cm$^{-1}$ |
| C≡C | 2100 cm$^{-1}$ |
| Allyl =C—H | 3080 cm$^{-1}$ |
| C=C | 1640 cm$^{-1}$ |
| def. | 990 cm$^{-1}$ |
| | 910 cm$^{-1}$ |
| aromatics | 1618 cm$^{-1}$ |
| | 1605 cm$^{-1}$ |
| | 1587 cm$^{-1}$ |
| | 1500 cm$^{-1}$ |
| Mass Spectrum: | in agreement. |

EXAMPLE 10

17α-acetyloxy-11β-[4-(1-propynyl)-phenyl]-19-nor-Δ$^{4,9}$-pregnadien-3,20-dione

Step A:
3,3-ethylenedioxy-11β-[4-(1-propynyl)-phenyl]-17α-hydroxy-19-nor-Δ$^9$-pregnaen-5α-ol-20-one (a) Preparation of magnesium compound 3 g of magnesium turnings and 10 ml of tetrahydrofuran were mixed and the reaction was started with a few drops of methyl bromide solution. Then 30 ml of a methyl bromide solution in tetrahydrofuran, titrating 100 mmoles/30 ml were added while maintaining reflux and the mixture was stirred for a further 15 minutes, then left at rest for 1 hour. Titre 2M/l.

(b) Condensation

Under an inert atmosphere, 2 g of 3,3-ethylenedioxy-11β-[4-(1-propynyl)-phenyl]-17α-trimethylsilyloxy-17α-cyano-Δ$^9$-estraene-5α-ol-were introduced rapidly in one lot into 25 ml of the magnesium compound solution previously obtained. The mixture was heated to reflux for 24 hours, then for a further 16 hours after concentrating to about 15 ml. After the return to ambient temperature, a fairly thick paste was obtained to which about 100 ml of ice and of ammonium chloride were added with caution. Extraction was carried out with ethyl acetate and the extracts were washed with salted water, dried, filtered and concentrated to dryness by distillation under reduced pressure. The residue was chromatographed over silica and eluted with a mixture of methylene chloride and ethyl acetate (8-2) to obtain 810 mg of 3,3-ethylenedioxy-11β-[4-(1-propynyl)-phenyl]-17α-hydroxy-19-nor-Δ$^9$-pregnaen-5α-ol-20-one.

IR Spectrum (chloroform)

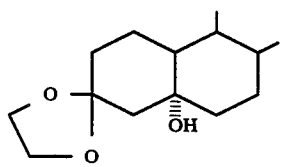

| | OH combined ketal | 3510 cm$^{-1}$ 1120 cm$^{-1}$ 1099 cm$^{-1}$ 1074 cm$^{-1}$ |
|---|---|---|

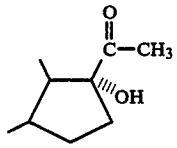

| | OH C=O | 3610 cm$^{-1}$ 1705 cm$^{-1}$ 1690 cm$^{-1}$ |
|---|---|---|

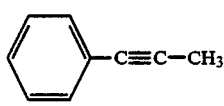

| | C≡C aromatic | 2255 cm$^{-1}$ 1558 cm$^{-1}$ 1508 cm$^{-1}$ |
|---|---|---|

NMR Spectrum (deuterochloroform)

| | |
|---|---|
| peak at 0.33 ppm | hydrogens of 18-Me |
| peak at 2.05 ppm | hydrogens of ≡C—CH$_3$ |
| peak at 2.22 ppm | hydrogens of COCH$_3$ |
| peak at 4.0 ppm | ketal |
| peaks at 4.3–4.35 ppm | hydrogens at 11 |
| peak at 3.35 ppm | hydrogens of OH |
| peaks at 7.07–7.17 ppm | } hydrogens of the |
| peaks at 7.24–7.33 ppm | aromatic nucleus. |

Step B:
11β-[4-(1-propynyl)-phenyl]-17α-hydroxy-19-nor-Δ$^{4,9}$-pregnadien-3,20-dione (deketalization, conjugation)

650 mg of 3,3-ethylenedioxy-11β-[4-(1-propynyl)-phenyl]-19-nor-Δ$^9$-pregnaen-5α,17α-diol-20-one, 10 ml of 96% ethanol and 1 ml of water were introduced under inert atmosphere and a solution was obtained by warming. 1 g of Redex CF resin was added, and the mixture was refluxed for 90 minutes. The resin was filtered off, and the filtrate was concentrated to dryness under reduced pressure. The residue was chromatographed over silica and eluted with a mixture of methylene chloride and ethyl acetate (8-2). The residue was taken up with ether, crystallization was initiated and the crystals were separated to obtain 355 mg of 11β-[4-(1-propynyl)-phenyl]-17α-hydroxy-19-nor-Δ$^{4,9}$-pregnadien-3,20-dione melting at 150° C.

IR Spectrum (chloroform)

| | OH C=O | 3608 cm$^{-1}$ + combined |
|---|---|---|
| | C=O C=C | 1706 cm$^{-1}$ 1690 cm$^{-1}$ 1655 cm$^{-1}$ 1600 cm$^{-1}$ |
| | C≡C aromatic | 2255 cm$^{-1}$ 1555 cm$^{-1}$ 1505 cm$^{-1}$ |

Step C:
11β-[4-(1-propynyl)-phenyl]-17α-acetoxy-19-nor-Δ$^{4,9}$-pregnadien-3,20-dione (acetylation)

490 mg of 11β-[4-(1-propynyl)-phenyl]-19-nor-Δ$^{4,9}$-pregnadien-17α-ol-3,20-dione and 7 ml of acetic acid were introduced under inert atmosphere and after solution, 2 ml of trifluoroacetic anhydride and 120 mg of p-toluene sulfonic acid were added with stirring at 20° C. for 3 hours. Then, the reaction mixture was poured into 100 ml of iced water and after separating and washing with water, the residue was taken up in methylene chloride, washed with an M aqueous solution of potassium bicarbonate, and with salted water, then dried and filtered. The filtrate was concentrated to dryness by distillation under reduced pressure and the residue was chromatographed over silica. Elution with a mixture of methylene chloride and ethyl acetate (9-1) and trituration with isopropyl ether yielded 300 mg of 11β-[4-(1-propynyl)-phenyl]-17α-acetoxy-19-nor-Δ$^{4,9}$-pregnadien-3,20-dione melting at 185° C. and having a specific rotation of $[\alpha]_D = +173°$ (c=0.5% in chloroform).

IR Spectrum (chloroform)

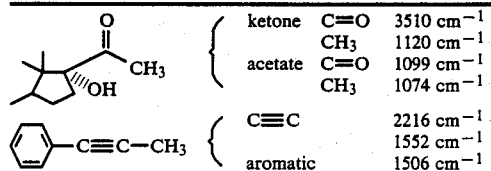

| | ketone | C=O | 3510 cm$^{-1}$ |
|---|---|---|---|
| | | CH$_3$ | 1120 cm$^{-1}$ |
| | acetate | C=O | 1099 cm$^{-1}$ |
| | | CH$_3$ | 1074 cm$^{-1}$ |

| | C≡C | 2216 cm$^{-1}$ |
|---|---|---|
| | | 1552 cm$^{-1}$ |
| | aromatic | 1506 cm$^{-1}$ |

EXAMPLE 11

17α-acetyloxy-11β-4-(ethynylphenyl)-19-nor-Δ$^{4,9}$-pregnadien-3,20-dione

Step A:
11β-(4-ethynylphenyl)-19-nor-Δ$^{4,9}$-pregnadien-17α-ol-3,20-dione

This stage is broken up in the following way:

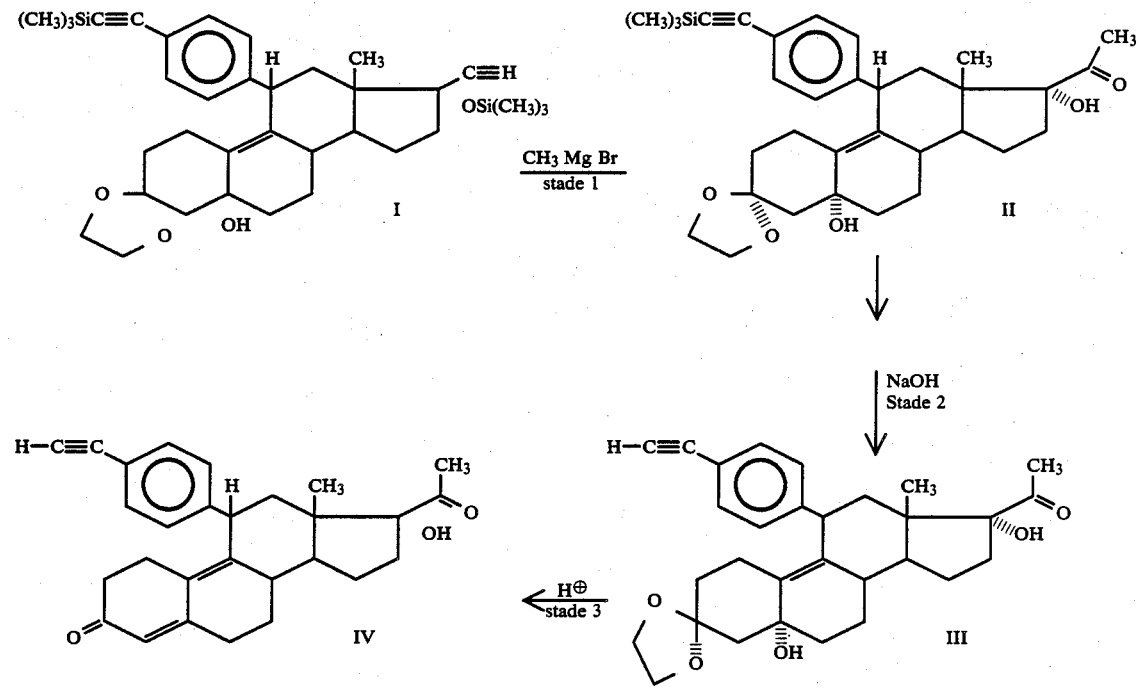

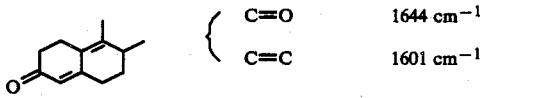

| | C=O | 1644 cm$^{-1}$ |
|---|---|---|
| | C=C | 1601 cm$^{-1}$ |

UV Spectrum
(ethanol)

| max. 246 nm E$_1^1$ = 483 | ε = 22700; |
|---|---|
| max. 255 nm E$_1^1$ = 493 | ε = 23200; |
| max. 300 nm E$_1^1$ = 409 | ε = 19200. |

Circular dichroism
(ethanol)

| infl. 247 nm | Δε = −21; |
|---|---|
| max. 256 nm | Δε = −25; |
| max. 301 nm | Δε = +21; |
| max. 354 nm | Δε = −0.68. |

NMR Spectrum
(deuterochloroform)

| peak at 0.31 ppm | hydrogens of 18-Me |
|---|---|
| peak at 2.04 ppm | hydrogens of ≡C—Me |
| peaks at 2.09–2.13 ppm | hydrogens of COMe |
| peaks at 4.42–4.5 ppm | hydrogens at 11 |
| peak at 5.83 ppm | hydrogens at 4 |
| peaks at 7.04–7.13 ppm | hydrogens of the aromatic nucleus. |
| peaks at 7.27–7.37 ppm | |

Stage 1:

1.2 g of magnesium turnings were introduced under inert atmosphere, and 20 ml of a 2.1M solution of methyl bromide in tetrahydrofuran were added slowly at 30° C. At the end of the introduction, the temperature was allowed to rise to 50° C. and then was allowed to return to 35° C. 1.79 g of 3,3-ethylenedioxy-11β-[4-trimethylsilylethynyl)phenyl]-17α-trimethylsilyloxy-17β-cyano-Δ$^9$-estrene-5α-ol were added and the solution was refluxed for 24 hours, cooled, and the reaction mixture was poured into 100 ml of a 10% aqueous solution of ammonium chloride. Extraction was carried out with ethyl acetate and the extracts were dried and filtered. The filtrate was concentrated to dryness and the residue was taken up with isopropyl ether, triturated and separated. The crystals were washed with isopropyl ether to obtain a first lot of 910 mg of steroid II. 120 mg of a second lot was obtained by evaporation of the mother liquors and treatment with isopropyl ether for a total of 1.03 g.

Stage 2:

1.03 g of steroid II, 20 ml of methanol and 2 ml of an N aqueous solution of sodium hydroxide were placed under inert atmosphere and the mixture was brought to 60° C., then cooled to 20° C. 2 ml of an N aqueous solution of hydrochloric acid were added and after concentrating under reduced pressure to half of the initial volume, the reaction mixture was poured into water and extracted with methylene chloride. The organic phase was washed with a 1M aqueous solution of potassium bicarbonate, dried, filtered, concentrated to dryness by distillation under reduced pressure to obtain 1 g of product which already contains a small amount of dienone IV.

Stage 3:

1 g of steroid III, 20 ml of methanol, 2 ml of water and 1.3 g of Redex CF resin, previously washed with methanol, were placed under inert atmosphere, and the mixture was refluxed for 1 hour with stirring. After filtering, the filtrate was concentrated to dryness by distillation under reduced pressure. The residue was chromatographed over silica and eluted with a mixture of methylene chloride and acetone (9-1). The useful fraction was concentrated and the residue was triturated with isopropyl ether to obtain 628 mg of steroid IV melting at 120°-140° C. (decomposition).

IR Spectrum (CHCl₃) OH free and combined: 3600 cm⁻¹ and 3500 cm⁻¹; H—C≡C: 3300 cm⁻¹; —C≡C—: 2100 cm⁻¹; C═O: 1700 cm⁻¹ shoulder and 1690 cm⁻¹; C═O conjugated: 1655 cm⁻¹; —C═C conjugated: 1600 cm⁻¹.

| NMR Spectrum (deuterochloroform) | |
|---|---|
| peak at 0.375 ppm | hydrogens of 18-Me |
| peak at 2.22 ppm | hydrogens of  |
| peak at 3.12 ppm | hydrogens of 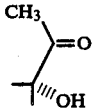 |
| peak at 3.0 ppm | hydrogens of H—C≡C— |
| peak at 4.37 ppm | hydrogens at 11 |
| peak at 5.75 ppm | hydrogens at 4 |
| peaks at 7.37–7.05 ppm | hydrogens of the aromatic nucleus. |

Step B:
17α-acetyloxy-11β-4-(ethynylphenyl)-19-nor-Δ⁴,⁹-pregnadien-3,20-dione 500 mg of 11β-(4-ethynylphenyl)-19-nor-Δ⁴,⁹-pregnadien-17β-ol-3,20-dione (steroid IV), 7 ml of acetic acid, 2 ml of trifluoroacetic anhydride and 120 mg of p-toluene sulfonic acid were placed under inert atmosphere and stirring for 90 minutes at ambient temperature. Then, the reaction mixture was poured into 100 ml of water and the precipitate formed was separated and washed with water. The solid was redissolved in 50 ml of methylene chloride and the organic solution was washed with an M aqueous solution of potassium bicarbonate. The organic phase was dried, filtered, and concentrated to dryness by distillation under reduced pressure. The residue was chromatographed over silica and eluted with a mixture of methylene chloride and ethyl acetate (9-1). The useful fraction was concentrated to dryness and the residue was triturated with isopropyl ether to obtain 295 mg of 17α-acetyloxy-11β-4-(ethynylphenyl)-19-nor-Δ⁴,⁹-pregnadien-3,20-dione melting >260° C. and having a specific rotation of [α]_D= +170.5° (c=0.4% in CHCl₃).

IR Spectrum (chloroform) H—C≡C: 3303 cm⁻¹; —C≡C—: 2108 cm⁻¹; C═O+C═conjugated: 1658 cm⁻¹ and 1605 cm⁻¹; C═O ketone: 1718 cm⁻¹; C═O acetate: 1733 cm⁻¹; aromatics: 1605 cm⁻¹, 1558 cm⁻¹, 1503 cm⁻¹, 840 cm⁻¹; methyl of the acetate: 1370 cm⁻¹; methyl of the acetone: 1355 cm⁻¹.

| NMR Spectrum (deuterochloroform) | |
|---|---|
| peak at 0.31 ppm | hydrogens of 18-Me |
| peak at 2.10 ppm | hydrogens of 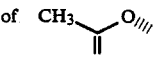 |
| peak at 2.13 ppm | hydrogens of 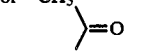 |
| peak at 3.05 ppm | hydrogens of H—C≡C— |
| peak at 4.45 ppm | hydrogens at 11 |
| peak at 5.80 ppm | hydrogens at 4 |
| peaks at 7.11–7.4 ppm | hydrogens of the aromatic nucleus. |

| UV Spectrum | |
|---|---|
| max. 243 nm | ε = 23400; |
| max. 252 nm | ε = 22900; |
| max. 300 nm | ε = 21200. |

EXAMPLE 12

11β-(4-ethynylphenyl)-17α-(3-hydroxy-1-propynyl)-Δ⁴,⁹-estradien-17β-ol-3-one

Step A:
3,3-ethylenedioxy-11β-[4-(2-trimethylsilylethynyl)-phenyl]-17β-[3-tetrahydropyranyloxy-1-propynyl]-estrene 5α,17β-diol-Δ⁹

840 mg of 3-tetrahydropyranyloxy-1-propyne and 25 ml of ether were mixed together and 3 ml of 1.65M n-butyllithium in hexane were added at 0° C. over about 15 minutes. The mixture was stirred for 15 minutes at 0° C. and 1.09 g of 3,3-ethylenedioxy-11β-[4-(2-trimethylsilyl-ethynyl)-phenyl]-Δ⁹-estraene-5α-ol-17-one of Step A of Example 4 in solution in 20 ml of tetrahydrofuran were added quickly. Stirring was carried out for 30 minutes at 0° C. and for 1 hour at 20° C. and the reaction mixture was poured into a saturated aqueous solution of ammonium chloride and extracted with ether. The extracts were dried and concentrated to dryness by distillation under reduced pressure. The residue was chromatographed over silica and elution with a mixture of methylene chloride and ethyl acetate (75-25) yielded 1.239 g of 11β-(4-ethynylphenyl)-17α-(3-hydroxy-1-propynyl)-Δ⁴,⁹-estradien-17β-ol-3-one.

IR Spectrum OH: 3599 cm⁻¹ and 3510 cm⁻¹; C≡C: 2230 cm⁻¹ and 2155 cm⁻¹; aromatics: 1600 cm⁻¹ and 1499 cm⁻¹.

| NMR Spectrum (CDCl₃) | |
|---|---|
| peak at 0.25 ppm: | hydrogens of trimethylsilyl methyls |
| peak at 0.47 ppm: | hydrogens of 18-Me |
| peak at 3.0 ppm: | hydrogens of hydroxyls |

NMR Spectrum (CDCl3)

| | |
|---|---|
| peak from 3.13 to 4.0 ppm: | hydrogens of 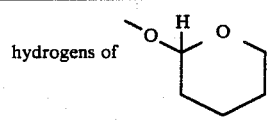 |
| peaks at 4.29–4.37 ppm: | hydrogens at 11 |
| peak at 3.7 ppm: | hydrogens of —C C—CH$_2$—O— methylene |
| peak at 3.97 ppm: | hydrogens of cyclic acetal methylenes |
| peak at 4.84 ppm: | hydrogen of 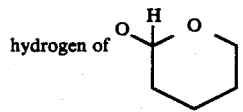 |
| peaks at 7.11–7.21 ppm and peaks at 7.34–7.44 ppm | hydrogens of (CH$_3$)$_3$—Si—C≡C— 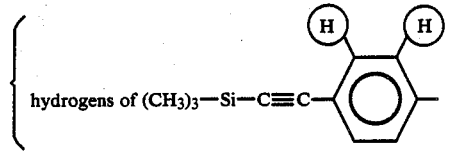 |

Step B:
11β-(4-ethynylphenyl)-17α-(3-hydroxy-1-propynyl)-Δ$^{4,9}$-estradien-17β-ol-3-one 500 mg of 3,3-ethylenedioxy-11β-[4-(2-trimethylsilylethynyl)phenyl]-17α-(3-tetrahydropyranyloxy-1-propynyl)-Δ$^9$-estraene-5α,17β-diol, and 5 ml of methanol were mixed together and 0.5 ml of a 2N aqueous solution of sodium hydroxide were added rapidly at 20° C. The resulting mixture was stirred for 30 minutes at 20° C. and 0.75 ml of a 2N aqueous solution of hydrochloric acid were added. The mixture was stirred for 5 hours at 20° C. and 0.5 ml of a saturated aqueous solution of potassium bicarbonate were added. Water was added and extraction was carried out with ethyl acetate. The extracts were dried and concentrated to dryness by distillation under reduced pressure. The residue was chromatographed over silica and eluted with a mixture of methylene chloride and ethyl acetate (75-25) to obtain 285 mg of crude product which was triturated in 3 ml of ether to obtain 201 mg of 11β-(4-ethynylphenyl)-17α-(3-hydroxy-1-propynyl-Δ$^{4,9}$-estradien-17β-ol-3-one melting at 120°–130° C.

| IR Spectrum (chloroform) | |
|---|---|
| OH: | 3605 cm$^{-1}$ |
| C≡C: | 2090 cm$^{-1}$ |
| ≡C—H: | 3302 cm$^{-1}$ |
| —C— conjugated: ‖ O | 1657 cm$^{-1}$ |
| C = conjugated: | 1602 cm$^{-1}$ |
| aromatic: | 1552 cm$^{-1}$ and 1503 cm$^{-1}$. |

UV Spectrum (ethanol)
max. 242 nm ε = 25000;
max. 251 nm ε = 23500;
max. 300 nm ε = 21100.

Circular Dichroism (ethanol)
220 nm Δε = +3.5;
245 nm Δε = −26;
252 nm Δε = −28;
296 nm Δε = +17;
315 nm Δε = +15
350 nm Δε = −0.9.
Analysis: C$_{29}$H$_{30}$O$_3$ (426.53)

Calculated: C % 81.66 H % 7.09
Found: 81.3 7.1

| NMR Spectrum (CDCl3) | |
|---|---|
| peak at 0.52 ppm: | hydrogens of 18-Me |
| peak at 3.07 ppm: | hydrogens of ethynyl |
| peak at 3.43 ppm: | hydrogens of hydroxyl |
| peak at 4.41 ppm: | hydrogens of —C≡C—CH$_2$—OH |
| peak at 4.39 ppm: | hydrogens at 11 |
| peak at 5.81 ppm: | hydrogens at 4 |
| peaks at 7.08–7.17 ppm and peaks at 7.39–7.47 ppm | hydrogens of H—C≡C— 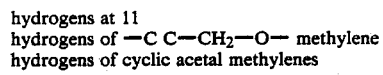 |

EXAMPLE 13

(E)

11β-(4-ethynylphenyl)-17α-(3-hydroxy-1-propenyl)-Δ$^{4,9}$-estradien-17β-ol-3-one

Step A:
3,3-ethylenedioxy-11β-[4-(2-trimethylsilylethynyl)-phenyl]-17α-(3-tetrahydropyranyloxy-1-propenyl)-Δ$^9$-estraene-5α,17β-diol 1.4 ml of tributyl tin hydride, 0.65 g of 3-tetrahydropyranyloxy-1-propyne and 6 mg of azoisobutyronitrile were mixed together, and heated to 65° C. After the reaction started, the temperature was maintained at 85°–90° C., allowed to return to 20° C. and 25 ml of tetrahydrofuran were added. The mixture was cooled to −65° C. and about 3 ml of 1.65M n-butyllithium in hexane were added over 5 minutes. Then, the mixture was stirred for 1 hour at −65° C. and 800 mg of the product of Step A of Example 4 were added. The temperature was allowed to return to 20° C. and the reaction mixture was poured into a saturated aqueous solution of ammonium chloride. Extraction was carried out by ethyl acetate and the extracts were dried and concentrated to dryness under reduced pressure. The residue was chromatographed over silica and eluted with a mixture of methylene chloride and acetone (90-10) to obtain 289 mg of 3,3-ethylenedioxy-11β-[4-(2-trimethylsilylethynyl)-phenyl]-17β-(3-tetrahydropyranyloxy-1-propenyl)-Δ⁹-estraene-5α,17β-diol.

IR Spectrum (chloroform) OH: 3600 cm⁻¹ and 3510 cm⁻¹; C≡C: 2155 cm⁻¹; aromatic: 1602 cm⁻¹, 1555 cm⁻¹ and 1500 cm⁻¹.

| NMR Spectrum (CDCl₃) | |
| --- | --- |
| peak at 0.24 ppm: | hydrogens of trimethylsilyl methyls |
| peak at 0.53 ppm: | hydrogens of 18-Me |
| peak at 3.4 ppm: | hydrogens of 11 |
| peak at 4.3 ppm: | hydrogens of 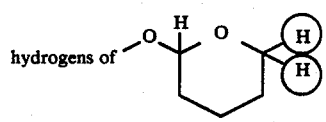 |
| peak at 4.66 ppm: | hydrogens of 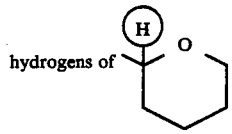 |
| peaks at 5.75 and 5.93 pm: | ethylene hydrogen (J = 15.5 Hz). |

Step B: (E) 11β-(4-ethynylphenyl)-17α-(3-hydroxy-1-propenyl)-Δ⁴,⁹-estradien-17β-ol-3-one 270 mg of the product of Step A and 3 ml of methanol were mixed together and 0.25 ml of a 2N aqueous solution of sodium hydroxide were added rapidly at 20° C. The mixture was stirred for 30 minutes at 20° C. and 0.35 ml of a 2N aqueous solution of hydrochloric acid were added with stirring for 7 hours at 20° C. An aqueous solution of potassium bicarbonate was added and water was added. Extraction was carried out with ethyl acetate and the extracts were dried and concentrated to dryness by distillation under reduced pressure. The residue was chromatographed over silica and elution with a mixture of methylene chloride and acetone (75-25) yielded 104 mg of (E) 11β-(4-ethynylphenyl)-17α-(3-hydroxy-1-propenyl)-Δ⁴,⁹-estradien-17β-ol-3-one with a specific rotation of [α]_D= +201° (c=0.4% in chloroform).

| IR Spectrum (chloroform) | |
| --- | --- |
| OH: | 3609 cm⁻¹ |
| ≡C—H: | 3302 cm⁻¹ |
| C≡C: | 2100 cm⁻¹ |
| —C— conjugated:<br>‖<br>O | 1657 cm⁻¹ |
| C=C conjugated: | 1602 cm⁻¹ |
| aromatic: | 1555 cm⁻¹ and 1503 cm⁻¹. |

UV Spectrum (ethanol)
max. 243 nm ε = 23200;
max. 253 nm ε = 22500;
max. 302 nm ε = 19900.
Circular Dichroism (ethanol)
219 nm Δε = +4;
245 nm Δε = −24;
252 nm Δε = −25.7;
298 nm Δε = +16;
317 nm Δε = +12.5;
351 nm Δε = −0.9.

| NMR Spectrum (CDCl₃) | |
| --- | --- |
| peak at 0.58 ppm: | hydrogens of 18-Me |
| peak at 3.07 ppm: | hydrogens of ethynyl |
| peak at 4.19 ppm: | hydrogens of 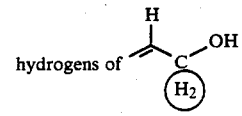 |
| peak at 4.41 ppm: | hydrogens at 11 |
| peaks from 5.82 to 5.93 ppm: | hydrogens at 4 and ethylene hydrogens |
| peaks at 7.1–7.2 ppm<br>peaks at 7.4–7.49 | } hydrogens of HC≡C— 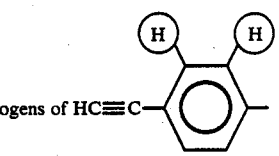 |

EXAMPLE 14 gamma-lactone of 11β-(4-ethynylphenyl)-19-nor-17α-Δ⁴,⁹-pregnadien-17β-ol-3-one-21-carboxylic acid Step A: gamma-lactone of 3,3-ethylenedioxy-11β-[4-(2-trimethylsilylethynyl)-phenyl]-19-nor-17α-Δ⁹-pregnaen-5α-ol-21-carboxylic acid 5.5 ml of 1.6M n butyllithium was mixed in hexane under inert atmosphere cooled to −70° C. and 15 ml of tetrahydrofuran were added over about 10 minutes at −70° C. Then dropwise at −70° C., 0.86 ml of [(CH₃)₂N]₂

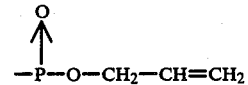

in solution in 5 ml of tetrahydrofuran were added with stirring for 30 minutes at −50° C. 1.08 g of 3,3-ethylene-dioxy-11β-[4-(2-trimethylsilylethynyl)-phenyl]-Δ⁹-estrene-5α-ol-17-one of Step A of Example 4 in solution in 7 ml of tetrahydrofuran were added over about 10 minutes. The temperature was allowed to return to 20° C. over about 20 minutes and stirring was maintained for 16 hours at 20° C. Then, the mixture was poured into a 1M aqueous solution of ammonium chloride and the pH was adjusted to 6 by 4 ml of a 2N aqueous solution of hydrochloric acid. Extraction was carried out with ethyl acetate and the extracts were dried and concentrated to dryness by distillation under reduced pressure. The residue was chromatographed over silica and eluted with a mixture of ether and acetone (9-1) to obtain 185 mg of gamma-lactone of 3,3-ethylenedioxy-11β-[4-(2-trimethylsilyl-ethynyl)-phenyl]-19-nor-17α-Δ⁹-pregnaen-5α-ol-21-carboxylic acid which was used as is for the following step.

IR Spectrum (chloroform) —C=O: 1763 cm⁻¹; OH: 3505 cm⁻¹; C≡C—Si: 2156 cm⁻¹.

| NMR Spectrum (CDCl₃) | |
| --- | --- |
| peak at 0.5 ppm: | hydrogens of 18-Me |
| peak at 0.23 ppm: | hydrogens of trimethylsilyl methyls |
| peak at 3.44 ppm: | hydrogens of hydroxyl at 5 |
| peak at 3.95 ppm: | hydrogens of cyclic acetal methyls |
| peaks at 4.27–4.36 ppm: | hydrogens at 11 |

| NMR Spectrum (CDCl₃) | |
|---|---|
| peaks at 7.08-7.18 ppm and peaks at 7.37-7.47 | hydrogens of 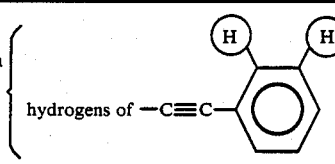 |

Step B: gamma-lactone of 11β-[4-(ethynylphenyl)]19-nor-Δ⁴,⁹-pregnadien-17β-ol-3-one-21-carboxylic acid 170 mg of gamma-lactone of 3,3-ethylenedioxy-11β-[4-(2-trimethyl-silylethynyl)-phenyl]-19-nor-17α-Δ⁹-pregnaen-5α-ol-21-carboxylic acid of Step A and 3 ml of methanol were mixed together and 0.35 ml of a 2N aqueous solution of sodium hydroxide was added at 20° C. over about 1 minute. After stirring for 30 minutes at 20° C., 0.5 ml of a 2N aqueous solution of hydrochloric acid were added followed by stirring for 2 hours at 20° C. An aqueous solution of potassium bicarbonate was added followed by water. Extraction was carried out with ethyl acetate and the extracts were dried and concentrated to dryness by distillation under reduced pressure. The residue was chromatographed over silica and eluted with a mixture of methylene chloride and acetone (93-7) to obtain 116 mg of gamma-lactone of 11β-[4-(ethynylphenyl)]-19-Δ⁴,⁹-pregnadien-17β-ol-3-one-21-carboxylic acid melting at 120°-130° C. and having a specific rotation of [α]=+97° (c=0.35% in chloroform).

| IR Spectrum (chloroform) | |
|---|---|
| C≡C—H: | 3306 cm⁻¹ |
| C≡C: | 2100 cm⁻¹ |
| 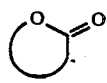 | 1767 cm⁻¹ |
| 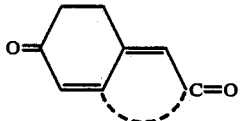 | 1658 cm⁻¹ |
| C=C: | 1603 cm⁻¹ |
| aromatics: | 1557 cm⁻¹ and 1500 cm⁻¹ |
| UV Spectrum (ethanol) | |
| max. 242 nm ε = 20400; | |
| max. 252 nm ε = 19500; | |
| max. 300 nm ε = 15600. | |
| Circular Dichroism (ethanol) | |
| 219 nm Δε = +6; | |
| 245 nm Δε = −18.5; | |
| 252 nm Δε = −20.2; | |
| 301 nm Δε = +17; | |
| 349 nm Δε = −0.7. | |
| NMR Spectrum (CDCl₃) | |
| peak at 0.6 ppm: | hydrogens of 18-Me |
| peaks at 4.4-4.49 ppm: | hydrogens at 11 |
| peak at 5.84 ppm: | hydrogens at 4 |

| peaks at 7.1-7.19 ppm and peaks at 7.41-7.5 | hydrogens of H—C≡C— 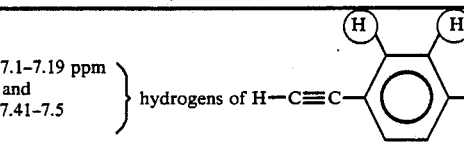 |
|---|---|

By using the processes described above in the description and in the examples given previously, the following products were obtained:

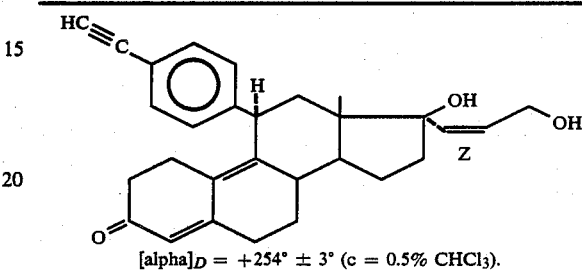

[alpha]$_D$ = +254° ± 3° (c = 0.5% CHCl₃).

| IR Spectrum (CHCl₃) | |
|---|---|
| OH free: | 3603 cm⁻¹; |
| combined: | 3410 cm⁻¹; |
| —C≡C—H: | 3302 cm⁻¹; |
| C=O conjugated: | 1657 cm⁻¹; |
| C=C conjugated: | 1602 cm⁻¹; |
| aromatics: | 1605 cm⁻¹ and 1504 cm⁻¹. |
| NMR Spectrum (CDCl₃) | |
| peak at 0.57 ppm: | hydrogens of 18-Me |
| peak at 3.06 ppm: | hydrogens of ethynyl |
| peak at 4.37 ppm: | hydrogens at 11 |
| peak at 5.78 ppm: | hydrogens at 4 |
| peaks at 7.11-7.41 ppm: | aromatic hydrogens |

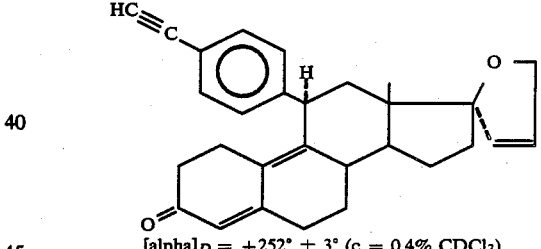

[alpha]$_D$ = +252° ± 3° (c = 0.4% CDCl₃)

| IR Spectrum (CHCl₃) | |
|---|---|
| No OH | |
| —C≡C—H: | 3302 cm⁻¹ |
| conjugated ketone: | 1657 cm⁻¹ and 1602 cm⁻¹ |
| C—O—C region: | 1081 cm⁻¹ and 1040 cm⁻¹ |
| NMR Spectrum (CDCl₃) | |
| peak at 0.56 ppm: | hydrogens of 18-Me |
| peak at 3.06 ppm: | hydrogens of ethynyl |
| peak at 4.35 ppm: | hydrogens at 11 |
| peak at 4.60 ppm: | O—CH₂— |
| peak at 5.82 ppm: | hydrogens at 4 |
| peaks at 7.16-7.45 ppm: | aromatic hydrogens. |

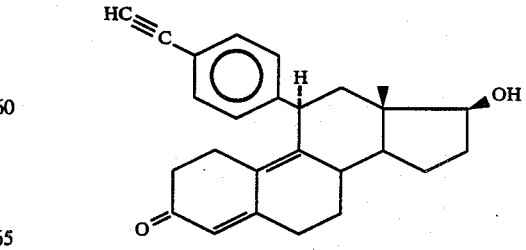

| NMR Spectrum (CDCl₃) | |
|---|---|
| peak at 0.416 ppm: | hydrogens of 18-Me |
| peak at 3.07 ppm: | hydrogens of ethynyl |

| | |
|---|---|
| peak at 3.66 ppm: | hydrogens at 17 |
| peak at 4.39 ppm: | hydrogens at 11 |
| peak at 5.81 ppm: | hydrogens at 4 |
| peaks at 7.13–7.50 ppm: | aromatic hydrogens. |

UV Spectrum (EtOH)
max. 244 nm ε = 21500
max. 253 nm ε = 20700
max. 302 nm ε = 19400

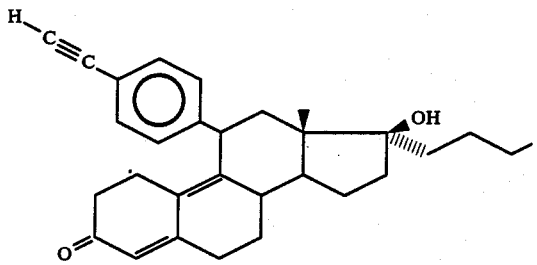

[alpha]$_D$ = +209.5 ± 3.5° (c = 0.5% CHCl$_3$)

NMR Spectrum (CDCl$_3$)
| | |
|---|---|
| peak at 0.52 ppm: | hydrogens of 18-Me |
| peak at 0.95 ppm: | hydrogens of CH$_3$ of the chain |
| peak at 3.07 ppm: | hydrogens of ethynyl |
| peak at 4.43 ppm: | hydrogens at 11 |
| peak at 5.81 ppm: | hydrogens at 4 |
| peak at 7.11–7.49 ppm: | aromatic hydrogens. |

UV Spectrum (EtOH)
max. 244 nm ε = 24300
max. 253 nm ε = 23400
max. 302 nm ε = 20700.

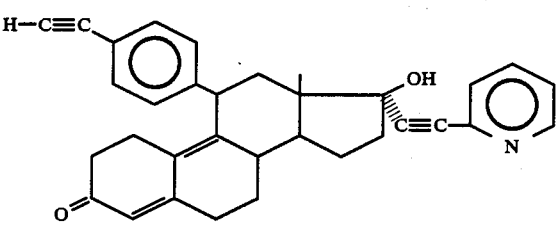

[alpha]$_D$ = +25° ± 1.5° (c = 0.5% CHCl$_3$)

NMR Spectrum (CDCl$_3$)
| | |
|---|---|
| peak at 0.566 ppm: | hydrogens of 18-Me |
| peak at 3.07 ppm: | hydrogens of ethynyl |
| peak at 4.45 ppm: | hydrogens at 11 |
| peak at 5.80 ppm: | hydrogens at 4 |
| peak at 8.64 ppm: | hydrogens H$_6$ of pyrroline |
| peaks at 7.13–7.81 ppm: | other aromatic hydrogens. |

UV Spectrum (EtOH)
max. 243 nm ε = 40600
infl. 252 nm
max. 280 nm ε = 23100
max. 287 nm ε = 24300
max. 303 nm ε = 21300.

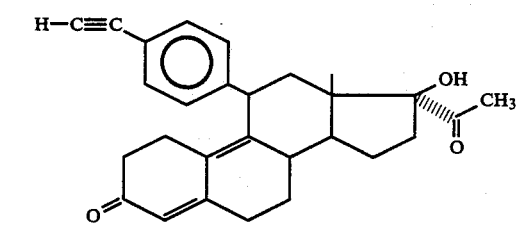

[alpha]$_D$ = +217° ± 4° (c = 0.6% CHCl$_3$)

NMR Spectrum (CDCl$_3$)
| | |
|---|---|
| peak at 0.588 ppm: | hydrogens of 18-Me |
| peak at 2.33 ppm: | hydrogens of 20-Me– |
| peak at 3.07 ppm: | hydrogens of ethynyl |
| peak at 4.33 ppm: | hydrogens at 11 |
| peak at 5.81 ppm: | hydrogens at 4 |
| peaks at 7.13–7.49 ppm: | aromatic hydrogens. |

UV Spectrum (EtOH)
max. 243 nm ε = 23800 max. 253 nm ε = 22900
max. 300 nm ε = 21300.

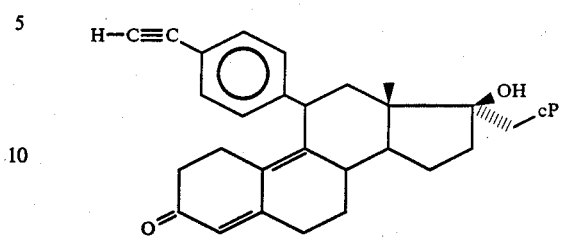

NMR Spectrum (CDCl$_3$)
| | |
|---|---|
| peak at 0.60 ppm: | hydrogens of 18-Me |
| peak at 3.07 ppm: | hydrogens of ethynyl |
| peaks from 3.57 to 3.92 ppm: | hydrogens of CH$_2$Cl |
| peak at 4.45 ppm: | hydrogens at 11 |
| peak at 5.83 ppm: | hydrogens at 4 |
| peaks at 7.12–8.63 ppm: | aromatic hydrogens. |

PHARMACOLOGICAL STUDY

Study of the activity upon the hormonal receptors.

A. Progestogen Receptor of the Rabbit Uterus

Non-adult rabbits of about 1 kg are given a cutaneous application of 25 μg of estradiol and 5 days after this treatment, the animals were sacrificed. The uteruses were removed, weighed and homogenized at 0° C. with the aid of a Potter polytertrafluoroethylene dish in a buffered TS solution (0.25M Tris 10 mM saccharose, HCl pH 7.4) (1 g of tissue per 50 ml of TS). The homogenate was then ultracentrifuged (105,000 g×90 mm) at 0° C. Aliquots of the supernatent fluid thus obtained were incubated at 0° C. for a period (t) with a constant concentration (T) of tritiated Product R (17, 21-dimethyl-19-nor-Δ$^{-4,9}$-pregnadien-3,20-dione) in the presence of increasing concentrations (0–2500. 10$^{-9}$M) either of R cold, or of progesterone cold, or of the product to be tested. The concentration of tritiated R bound (B) was then measured in each incubate by the technique of adsorbtion on dextran charcoal.

B. Gluoccocorticoid Receptor of the Rat Thymus

Male Sprague Dawley EOPS rats of 160 to 200 g were surrenalectomised and 4 to 8 days after this ablation, the animals were sacrificed. The thymuses were removed and homogenized at 0° C. in a 10 mM Tris, 0.25M saccharose, 2 mM dithiothreitol, HCl pH 7.4 buffer with the aid of a Potter polytetrafluoroethylene dish (1 g of tissue per 10 ml of TS). The homogenate was then ultracentrifuged (105,000×90 mn) at 0° C. Aliquots of the supernatent fluid thus obtained were incubated at 0° for a period (t) with a constant concentration (T) of tritiated dexamethasone in the presence of increasing concentrations (0–2500. 10$^{-9}$M) either of cold dexamethasone, or of cold product to be tested. The concentration of tritiated dexamethasone bound (B) was then measured in each incubate by the technique of adsorption on dextran charcoal.

Calculation of the Relative Bonding Affinity

The calculation of the relative bonding affinity (ARL) was identical for all the receptors.

The 2 curves were plotted as follows: the percentage of the tritiated hormone bound B/T as a function of the logarithm of the concentration of the reference hormone cold and B/T as a function of the logarithm of the concentration of the product tested cold.

The straight line of the equation $I_{50}=(B/T\ max+B/T\ min)/2$. B/T max = percentage of the tritiated hormone bound for one incubation of this tritiated hormone at the concentration (T) was determined. B/T min = percentage of the tritiated hormone bound for one incubation of this tritiated hormone at the concentration (T) in the presence of a great excess of the cold hormone ($2500 \cdot 10^{-9}$M).

The intersections of the straight line $I_{50}$ and of the curves make it possible to estimate the concentrations of the cold reference hormone (CH) and of the cold product tested (CX) which inhibits 50% of the bonding of the tritiated hormone on the receptor. The relative affinity of the bonding (ARL) of the product tested was determined by the equation $$ARL = 100 \frac{(CH)}{(CX)}$$

The results obtained are as follows:

| Product of the Example Time of incubation at 0° | Progestogen | | Glucocorticoid | |
|---|---|---|---|---|
| | 2H | 24H | 4H | 24H |
| Product of Example 3 | 44 | 167 | 107 | 124 |
| Product of Example 4 | 41 | 124 | 65 | 57 |
| Product of Example 5 | 51 | 325 | 84 | 153 |
| Product of Example 8 | 38 | 285 | 175 | 233 |

CONCLUSION

The products studied and especially the products of Examples 3, 4, 5 and 8 possess a very marked affinity for the gluococorticold and progestogen receptors. From the said results, one can conclude that the products display an agonistic activity to the antagonist of glucocorticoids and of protestogens.

C. Antiglucocorticoidal Activity

The technique employed was derived from the method described by Daune et al in Molecular Pharmacology, Vol. 13, 948–955 (1977) "The relationship between glucocorticold structure and effects upon thymocytes", for the thymocytes of the mouse. The thymocytes of surrenalectomised rats were incubated at 37° C. for 3 hours in a nutrient medium containing $5 \cdot 10^{-8}$M of dexamethasone, in the presence or absence of a product to be studied at different concentrations. One added tritiated uridine, and continued the incubation for one hour. The incubates were cooled and treated with a 5% solution of trichloroacetic acid. After filtration on Whatman GF/A paper, and washing three times with a 5% trichloroacetic acid solution, the radioactivity retained by the filter was determined. The glucocorticoids and, in particular dexamethasone, cause a diminution of the incorporation of tritiated uridine. The products tested and more especially the products of Examples 4, 5 and 8 oppose this effect.

| Product of Example | $5 \cdot 10^{-8}$ Dexamethasone and product tested | % inhibition of the effect of Dexamethasone |
|---|---|---|
| 4 | $10^{-8}$M | 46 |
| | $10^{-7}$M | 71 |
| | $10^{-6}$M | 99 |
| 5 | $10^{-8}$M | 47 |
| | $10^{-7}$M | 84 |
| | $10^{-6}$M | * |
| 8 | $10^{-8}$M | 7 |
| | $10^{-7}$M | 37 |
| | $10^{-6}$M | 77 |

*At the dosage level of $10^{-6}$M, the inhibition of the effect of methasone was absolute.

It has furthermore been established that employed alone, the products tested do not cause any glucocorticoid-type effect.

CONCLUSION

The products studied display a very marked antiglucocorticoid activity while being bereft of a glucocorticoid activity.

D. Abortifacient Activity in the rat

Day D 1 of gestation was determined by the presence of spermatozoids in the vaginal smears and on Day D 9 of gestation, the product was administered orally in suspension in carboxymethyl cellulose containing 0.5% of Tween. The animals were sacrificed 72 hours after the treatment and the uterus was examined to determine the state of gestation. A complete abortion in all the animals of the group treated with the products of Examples 3, 4, 5 and 8 administered at a dosage level of 3 mg/kg was observed.

Pharmaceutical Compositions

Tablets have been prepared according to the following formula: 50 mg of Product of Example 5 and Excipient of talc, starch, magnesium stearate sufficient for a finished tablet of 120 mg.

Various modifications of the products and methods of the invention may be made without departing from the spirit or scope thereof and it should be understood that the invention is intended to be limited only as defined in the appended claims.

What we claim is:

1. A compound selected from the group consisting of 11β-alkynylphenyl-19-nor-steroids of the formula

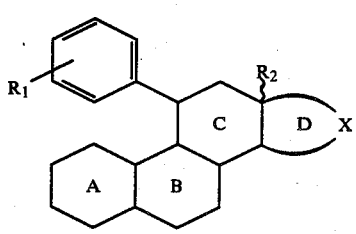

wherein $R_1$ is alkynyl of 2 to 8 carbon atoms optionally substituted with at least one member of the group consisting of —OH, halogen, trialkylsilyl of 1 to 6 alkyl carbon atoms, alkoxy and alkylthio of 1 to 6 carbon atoms and dialkylamino of 1 to 6 alkyl carbon atoms, $R_2$ is alkyl of 1 to 3 carbon atoms, the A and B rings have a structure selected from the group consisting of

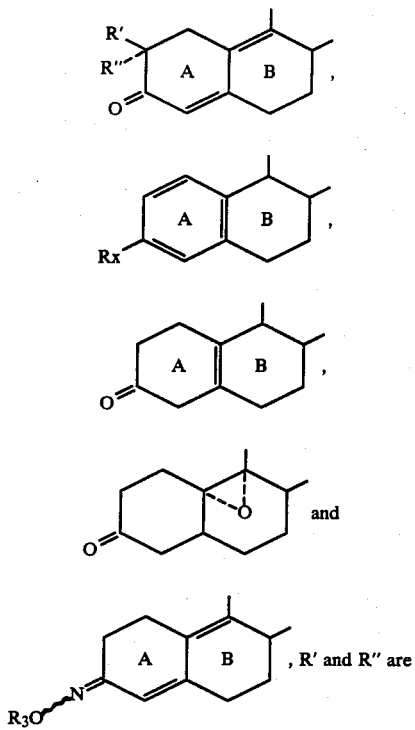

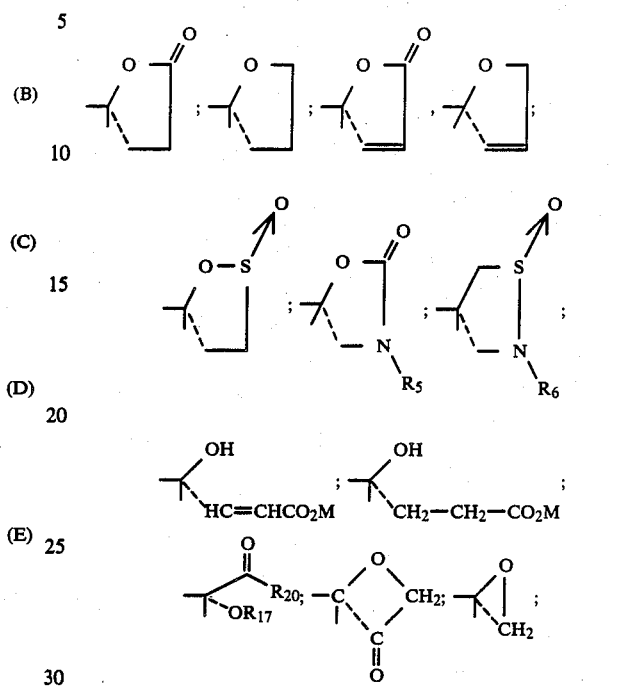

individually selected from the group consisting of hydrogen and alkyl of 1 to 4 carbon atoms, Rx is selected from the group consisting of hydrogen, or ORe in which Re is selected from the group consisting of hydrogen, alkyl of 1 to 6 carbon atoms and acyl, R$_3$ is selected from the group consisting of hydrogen, alkyl of 1 to 8 carbon atoms are aralkyl of 7 to 15 carbon atoms, the group

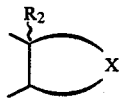

is selected from the group consisting of

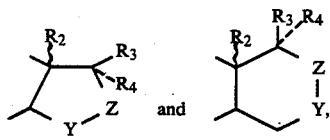

R$_3$ and R$_4$ are individually selected from the group consisting of hydrogen, hydroxy, —OAlk$_4$,

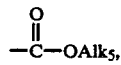

alkyl of 1 to 8 carbon atoms, alkenyl and alknynyl of 2 to 8 carbon atoms, phenyl, benzyl, phenethyl, thienyl, furyl, aralkenyl and aralkynyl, the latter seven being unsubstituted or substituted with at least one member of the group consisting of hydroxy, alkoxy and alkylthio of 1 to 4 carbon atoms, halogen and dialkylamino of 1 to 6 alkyl carbon atoms, Alk$_4$ and Alk$_5$ being individually selected from the group consisting of alkyl of 1 to 8 carbon atoms and benzyl or R$_3$ and R$_4$ taken together form a member of the group consisting of R$_5$ and R$_6$ are hydrogen or alkyl of 1 to 4 carbon atoms, M is hydrogen, lithium, sodium or potassium, R$_{20}$ is alkyl of 1 to 8 carbon atoms unsubstituted or substituted with hydroxy, R$_{17}$ is selected from the group consisting of hydrogen and acetyl, Z and Y form a group selected from the group consisting of

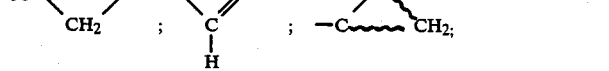

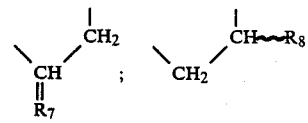

R$_7$ and R$_8$ are individually alkyl of 1 to 4 carbon atoms and the wavy lines indicate that R$_2$, R$_7$ and R$_8$ and the —CH$_2$— can be in either possible configuration and their non-toxic, pharmaceutically acceptable salts with acids and bases.

2. A compound of claim 1 having the formula

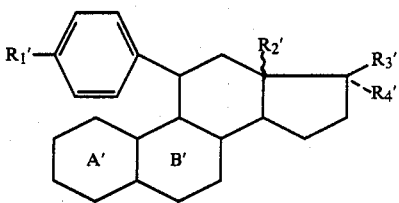

wherein $R_1'$ is alkynyl of 2 to 4 carbon atoms optionally substituted by a member of the group consisting of hydroxyl, halogen, and trimethylsilyl, $R_2'$ is methyl or ethyl, $R_3'$ and $R_4'$ are individually selected from the group consisting of hydroxyl, acetoxy, alkyl of 1 to 8 carbon atoms, alkenyl and alkynyl of 2 to 8 carbon atoms, the last 3 being optionally substituted by hydroxyl or halogen or $R_3'$ and $R_4'$ taken together form

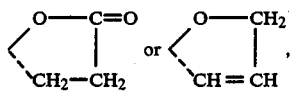

the A' and B' rings are selected from the group consisting of (A)

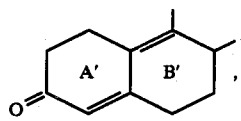

(B)

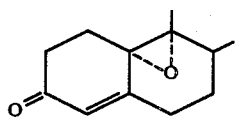

and (C)

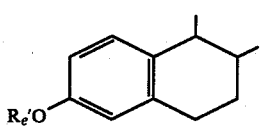

and $R_e'$ is hydrogen or alkyl of 1 to 4 carbon atoms.

3. A compound of claim 2 wherein $R_1'$ is —C≡C—$R_{11}$, $R_{11}$ is selected from the group consisting of hydrogen, methyl and trimethylsilyl, $R_3'$ and $R_4'$ are selected from the group consisting of (a) hydroxyl, (b) acetoxy (c) ethynyl and propynyl optionally substituted by halogen or —OH and (d) propyl and propenyl optionally substituted with —OH or $R'_3$ and $R'_4$ taken together form

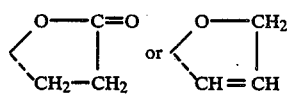

4. A compound of claim 1 which is 11β-(4-ethynylphenyl)-17α-(1-propynyl)-Δ⁴,⁹-estradiene-17β-ol-3-one.

5. A compound of claim 1 which is 11β-(4-ethynylphenyl)-17α-allyl-Δ⁴,⁹-estradiene-17β-ol-3-one.

6. A compound of claim 1 which is 11β-(4-ethynylphenyl)-17α-chloroethynyl-Δ⁴,⁹-estradiene-17β-ol-3-one.

7. A compound of claim 1 which is 9α,10α-epoxy-11β-(4-ethynylphenyl)-17α-chloroethynyl-Δ⁴-estrene-17β-ol-3-one.

8. An antiprogestomimetic and antiglucocorticoidal composition comprising an antiprogestomimetically and antigluococorticoidally effective amount of at least one compound of claim 1.

9. A composition of claim 8 wherein the compound has the formula

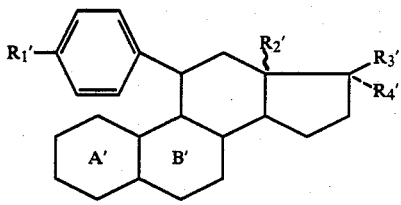

wherein $R_1'$ is alkynyl of 2 to 4 carbon atoms optionally substituted by a member of the group consisting of hydroxyl, halogen, and trimethylsilyl, $R_2'$ is methyl or ethyl, $R_3'$ and $R_4'$ are individually selected from the group consisting of hydroxyl, acyloxy, alkyl of 1 to 8 carbon atoms, alkenyl and alkynyl of 2 to 8 carbon atoms, the last 3 being optionally substituted by hydroxyl or halogen or $R_3'$ and $R_4'$ taken together form

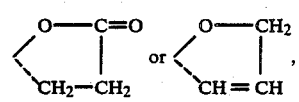

the A' and B' rings are selected from the group consisting of (A)

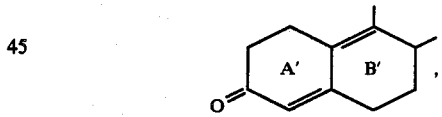

(B)

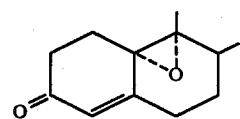

and (C)

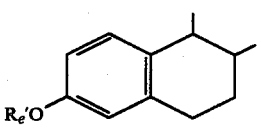

and $R_e'$ is hydrogen or alkyl of 1 to 4 carbon atoms.

10. A composition of claim 9 wherein $R_1'$ is —C≡C—$R_{11}$, $R_{11}$ is selected from the group consisting of hydrogen, methyl and trimethylsilyl, R3' and R4' are selected from the group consisting of (a) hydroxyl, (b) acetoxy, (c) ethynyl and propynyl optionally substituted by halogen or —OH and (d) propyl and propenyl optionally substituted with —OH or R3' and R4' taken together form

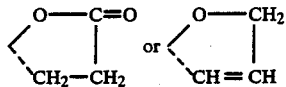

11. A composition of claim 8 wherein the active compound is 11β-(4-ethynylphenyl)-17α-(1-propynyl)-Δ⁴,⁹-estradiene-17β-ol-3-one.

12. A composition of claim 8 wherein the active compound is 11β-(4-ethynylphenyl)-17α-allyl-Δ⁴,⁹-estradiene-17β-ol-3-one.

13. A composition of claim 8 wherein the active compound is 11β-(4-ethynylphenyl)-17α-chloroethynyl-Δ⁴,⁹-estradiene-17β-ol-3-one.

14. A composition of claim 8 wherein the active compound is 9α,10α-epoxy-11β-(4-ethynylphenyl)-17α-chloroethynyl-Δ⁴-estrene-17β-ol-3-one.

15. A method of inducing antiprogestomimetic and antiglucocorticoid activity in warm-blooded animals comprising administering an antiprogestomimetically and antiglucocorticoidally effective amount of at least one compound of claim 1.

16. A method of claim 15 wherein the compound has the formula

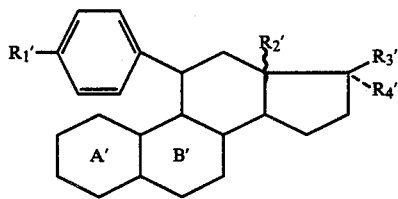

wherein R1' is alkynyl of 2 to 4 carbon atoms optionally substituted by a member of the group consisting of hydroxyl, halogen, and trimethylsilyl, R2' is methyl or ethyl, R3' and R4' are individually selected from the group consisting of hydroxyl, acyloxy, alkyl of 1 to 8 carbon atoms, alkenyl and alkynyl of 2 to 8 carbon atoms, the last 3 being optionally substituted by hydroxyl or halogen or R3' and R4' taken together form

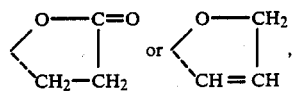

the A' and B' rings are selected from the group consisting of (A)

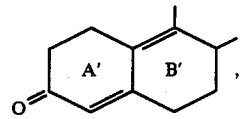

(B)

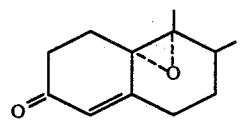

and (C)

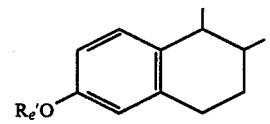

and R3' is hydrogen or alkyl of 1 to 4 carbon atoms.

17. A method of claim 16 wherein R1' is —C≡C—R11, R11 is selected from the group consisting of hydrogen, methyl and trimethylsilyl, R3' and R4' are selected from the group consisting of (a) hydroxyl, (b) acetoxy, (c) ethynyl and propynyl optionally substituted by halogen or —OH and (d) propyl and propenyl optionally substituted with —OH or R3' and R4' taken together form

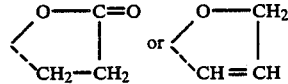

18. A method of claim 15 wherein the compound is 11β-(4-ethynylphenyl)-17α-(1-propynyl)-Δ⁴,⁹-estradiene-17β-ol-3-one.

19. A method of claim 15 wherein the compound is 11β-(4-ethynylphenyl)-17α-allyl-Δ⁴,⁹-estradiene-17β-ol-3-one.

20. A method of claim 15 wherein the compound is 11β-(4-ethynylphenyl)-17α-chloroethynyl-Δ⁴,⁹-estradiene-17β-ol-3-one.

21. A method of claim 15 wherein the compound is 9α,10α-epoxy-11β-(4-ethynylphenyl)-17α-chloroethynyl-Δ⁴-estrene-17β-ol-3-one.

* * * * *